US009339552B2

(12) United States Patent  
Kisak et al.

(10) Patent No.: US 9,339,552 B2  
(45) Date of Patent: *May 17, 2016

(54) DICLOFENAC TOPICAL FORMULATION

(71) Applicant: HZNP Limited, Hamilton Pembroke (BM)

(72) Inventors: Ed Kisak, San Diego, CA (US); Jagat Singh, Toronto (CA)

(73) Assignee: HZNP Limited, Pembroke (BM)

( * ) Notice: Subject to any disclaimer, the term of this patent is extended or adjusted under 35 U.S.C. 154(b) by 0 days.

This patent is subject to a terminal disclaimer.

(21) Appl. No.: 14/922,903

(22) Filed: Oct. 26, 2015

(65) Prior Publication Data

US 2016/0045605 A1    Feb. 18, 2016

Related U.S. Application Data

(63) Continuation of application No. 14/705,649, filed on May 6, 2015, now Pat. No. 9,220,784, which is a continuation of application No. 14/497,096, filed on Sep. 25, 2014, now Pat. No. 9,066,913, which is a continuation of application No. 14/025,781, filed on Sep. 12, 2013, now Pat. No. 8,871,809, which is a continuation of application No. 13/564,688, filed on Aug. 1, 2012, now Pat. No. 8,563,613, which is a continuation of application No. 12/134,121, filed on Jun. 5, 2008, now Pat. No. 8,252,838, which is a continuation of application No. PCT/US2007/081674, filed on Oct. 17, 2007.

(60) Provisional application No. 60/829,756, filed on Oct. 17, 2006.

(51) Int. Cl.
| | |
|---|---|
| *A01N 37/12* | (2006.01) |
| *A61K 47/38* | (2006.01) |
| *A61K 9/00* | (2006.01) |
| *A61K 31/196* | (2006.01) |
| *A61K 47/20* | (2006.01) |
| *A61K 47/10* | (2006.01) |

(52) U.S. Cl.
CPC .............. *A61K 47/38* (2013.01); *A61K 9/0014* (2013.01); *A61K 31/196* (2013.01); *A61K 47/10* (2013.01); *A61K 47/20* (2013.01)

(58) Field of Classification Search
CPC ..... A61K 47/38; A61K 9/0014; A61K 47/10; A61K 47/20; A61K 31/196
See application file for complete search history.

(56) References Cited

U.S. PATENT DOCUMENTS

| | | | |
|---|---|---|---|
| 3,711,602 A | 1/1973 | Herschler | |
| 3,740,420 A | 6/1973 | Herschler et al. | |
| 3,740,421 A | 6/1973 | Schmolka et al. | |
| 4,296,104 A | 10/1981 | Herschler et al. | |
| 4,309,414 A | 1/1982 | Inagi et al. | |
| 4,342,784 A | 8/1982 | Havemeyer et al. | |
| 4,441,739 A | 4/1984 | Cluff et al. | |
| 4,543,251 A | 9/1985 | Kamishita | |
| 4,575,515 A | 3/1986 | Sandborn | |
| 4,652,557 A | 3/1987 | Sandborn | |
| 4,670,254 A | 6/1987 | Kamishita | |
| 4,707,354 A | 11/1987 | Garlen et al. | |
| 4,855,294 A | 8/1989 | Patel et al. | |
| 4,871,767 A | 10/1989 | Beckermann et al. | |
| 5,350,769 A | 9/1994 | Kasai et al. | |
| 5,374,661 A | 12/1994 | Betlach, II | |
| 5,422,102 A | 6/1995 | Ikeda et al. | |
| 5,674,912 A | 10/1997 | Martin | |
| 5,874,479 A | 2/1999 | Martin | |
| 5,976,566 A | 11/1999 | Samour et al. | |
| 6,211,250 B1 | 4/2001 | Tomlinson et al. | |
| 6,387,383 B1 | 5/2002 | Dow et al. | |
| 6,399,093 B1 | 6/2002 | Petrus | |
| 6,750,291 B2 | 6/2004 | Kim et al. | |
| 8,217,078 B1 | 7/2012 | Sinqh et al. | |
| 8,252,838 B2 | 8/2012 | Kisak et al. | |
| 8,546,450 B1 | 10/2013 | Singh et al. | |
| 8,618,164 B2 | 12/2013 | Singh et al. | |
| 2002/0012695 A1 | 1/2002 | Lee et al. | |
| 2002/0197292 A1 | 12/2002 | Fowler | |
| 2003/0082226 A1 | 5/2003 | Samour et al. | |
| 2003/0161867 A1 | 8/2003 | Lu et al. | |
| 2004/0175415 A1 | 9/2004 | Chan et al. | |
| 2004/0213744 A1 | 10/2004 | Lulla et al. | |
| 2004/0222123 A1 | 11/2004 | Niemann | |
| 2005/0239894 A1 | 10/2005 | Steiger | |
| 2006/0067985 A1 | 3/2006 | Dierking et al. | |
| 2006/0148903 A1 | 7/2006 | Burch et al. | |
| 2007/0053984 A1 | 3/2007 | Spann-Wade et al. | |
| 2007/0141182 A1 | 6/2007 | Niazi | |
| 2007/0280972 A1 | 12/2007 | Zhang et al. | |
| 2008/0300311 A1 | 12/2008 | Kisak et al. | |
| 2009/0131447 A1 | 5/2009 | Kamboi et al. | |

FOREIGN PATENT DOCUMENTS

| | | |
|---|---|---|
| DE | 20319986 | 4/2004 |
| EP | 0 245 126 | 11/1987 |

(Continued)

OTHER PUBLICATIONS

Alberti, I., et al. "Pharmaceutical development and clinical effectiveness of a novel gel technology for transdermal drug delivery," Expert Opin. Drug Deliv. 2005, 2(5), 935-950.

An article entitled "Other articles noted" by Evidence-Based Medicine, 2005, 10:63-64.

Anchordoguy, T.J., "Temperature-dependent perturbation of phospholipid bilayers by dimethylsulfoxide," Biochimica et Biophysica Acta, 1992, 1104:117-122.

ANDA Notice Letter, Watson Laboratories, Inc. to Mallinckrodt Inc. and HZNP Limited. Re: Notification of Certification for U.S. Pat. Nos. 8,217,078, 8,252,838, 8,546,450, 8,563,613, 8,618,164 and 8,741,956 Pursuant to § 505G)(2)(B)(iv) of the Federal Food, Drug, and Cosmetic Act. Nov. 12, 2014.

(Continued)

*Primary Examiner* — Suzanne Ziska

(57) ABSTRACT

The present invention provides a gel formulation comprising diclofenac sodium which has superior transdermal flux properties, which may be used for the topical treatment of pain, such as in osteoarthritis.

14 Claims, 12 Drawing Sheets

(56) References Cited

FOREIGN PATENT DOCUMENTS

| | | |
|---|---|---|
| EP | 0 450 123 | 10/1991 |
| JP | 61-254519 | 11/1986 |
| JP | 61-277613 | 12/1986 |
| JP | 62-263122 | 11/1987 |
| JP | 63-83023 | 4/1988 |
| JP | 3-291222 | 12/1991 |
| JP | 2001-513543 | 9/2001 |
| WO | WO 97/13528 | 4/1997 |
| WO | WO 99/09954 | 3/1999 |
| WO | WO 03/094905 | 11/2003 |
| WO | WO 2004/017998 | 3/2004 |
| WO | WO 2005/009510 | 2/2005 |
| WO | WO 2006/096360 | 9/2006 |
| WO | WO 2007/010559 | 1/2007 |
| WO | WO 2007/016766 | 2/2007 |
| WO | WO 2007/089617 | 8/2007 |
| WO | WO 2008/049020 | 4/2008 |
| WO | WO 2008/088827 | 7/2008 |
| WO | WO 2010/060798 | 6/2010 |

OTHER PUBLICATIONS

ANDA Notice Letter, Paddock Laboratories, LLC to Mallinckrodt Inc. and HZNP Limited. Re: Notification of Certification of Invalidity, Unenforceability, and/or NonInfringement for U.S. Pat. Nos. 8,217,078, 8,252,838, 8,546,450, 8,563,613, 8,618,164, and 8,741,956 Pursuant to § 505(j)(2)(B)(iv) of the Federal Food, Drug, and Cosmetic Act. Dec. 1, 2014.

ANDA Notice Letter, Taro Pharmaceuticals, USA, Inc. and Taro Pharmaceutical Industries, Ltd. to Mallinckrodt Inc. and HZNP Limited. Re: Notification Pursuant to the Federal Food, Drug, and Cosmetic Act (21 U.S.C. 355U)(2)(B)(ii) and 21 C.F.R. § 314.95): ANDA No. 208098, U.S. Pat. Nos. 8,217,078, 8,252,838, 8,546,450, 8,563,613, 8,618,164, 8,741,956, and 8,871,809; PENNSAID (Diclofenac Sodium 2.0%). Jan. 30, 2015.

ANDA Notice Letter, Taro Pharmaceuticals, USA, Inc. and Taro Pharmaceutical Industries, Ltd. to Mallinckrodt Inc. and HZNP Limited. Re: Notification Pursuant to the Federal Food, Drug, and Cosmetic Act (21 U.S.C. 355U)(2)(B)(ii) and 21 C.F.R. § 314.95): ANDA No. 208098, U.S. Pat. Nos. 9,066,913 and 9,101,591; PENNSAID (Diclofenac Sodium 2.0%). Sep. 17, 2015.

ANDA Notice Letter, Taro Pharmaceuticals, USA, Inc. and Taro Pharmaceutical Industries, Ltd. to Mallinckrodt Inc. and HZNP Limited. Re: Notification Pursuant to the Federal Food, Drug, and Cosmetic Act (21 U.S.C. 355U)(2)(B)(ii) and 21 C.F.R. § 314.95): ANDA No. 208098, U.S. Pat. Nos. 9,066,913, 9,101,591, and 9,132,110; PENNSAID (Diclofenac Sodium 2.0%). Sep. 21, 2015.

ANDA Notice Letter, Lupin Limited to Nuvo Research Inc., Paladin Labs, Ltd., Mallinckrodt Inc. and Horizon Pharma. Re: Notice of Paragraph IV Certification Regarding NDA 204623 (Diclofenac Sodium Solution Topical 2%) with respect to U.S. Pat. Nos. 8,217,078, 8,252,838, 8,546,450, 8,563,613, 8,618,164, 8,741,956, and 8,871,809. Mar. 17, 2015.

ANDA Notice Letter, Lupin Limited to HZNP Limited. RE: Notice of Paragraph IV Certification of U.S. Pat. Nos. 8,217,078; 8,252,838; 8,546,450; 8,563,613; 8,618,164; 8,741,956 and 8,871,809, Concerning ANDA 208021 for Diclofenac Sodium Topical Solution, 2%, Mar. 17, 2015.

ANDA Notice Letter, Lupin Limited to Mallinckrodt, Inc., Nuvo Research Inc., Padin Labs Inc., and HZNP Limited. RE: Notice of Paragraph IV Certification of U.S. Pat. No. 9,066,913, Concerning ANDA 204623 for Diclofenac Sodium Topical Solution, 2%, Jul. 10, 2015.

ANDA Notice Letter, Lupin Limited to Mallinckrodt, Inc., Nuvo Research Inc., Padin Labs Inc., and HZNP Limited. RE: Notice of Paragraph IV Certification of U.S. Pat. No. 9,101,591, Concerning ANDA 204623 for Diclofenac Sodium Topical Solution, 2%, Aug. 27, 2015.

ANDA Notice Letter, Paddock Laboratories, LLC to Mallinckrodt Inc. and HZNP Limited. Re: Notification of Certification of Invalidity, Unenforceability, and/or NonInfringement for U.S. Pat. No. 8,871,809 Pursuant to § 505(j)(2)(B)(iv) of the Federal Food, Drug, and Cosmetic Act.

ANDA Notice Letter, Paddock Laboratories, LLC to Mallinckrodt Inc. and HZNP Limited. Re: Notification of Certification of Invalidity, Unenforceability, and/or NonInfringement for U.S. Pat. No. 9,066,913, Pursuant to § 505(j)(2)(B)(iv) of the Federal Food, Drug, and Cosmetic Act. Jul. 16, 2015.

ANDA Notice Letter, Paddock Laboratories, LLC to Mallinckrodt Inc. and HZNP Limited. Re: Notification of Certification of Invalidity, Unenforceability, and/or NonInfringement for U.S. Pat. No. 9,101,591, Pursuant to § 505(j)(2)(B)(iv) of the Federal Food, Drug, and Cosmetic Act. Sep. 11, 2015.

ANDA Notice Letter, Actavis Laboratories UT, Inc. to Mallinckrodt Inc., Nuvo Research Inc. and HZNP Limited. Re: Notification of Certification for U.S. Pat. No. 8,871,809 Pursuant to § 505(j)(2)(B)(iv) of the Federal Food, Drug, and Cosmetic Act. Mar. 25, 2015.

ANDA Notice Letter, Actavis Laboratories UT, Inc. to Mallinckrodt Inc. and HZNP Limited. Re: Notification of Certification for U.S. Pat. No. 9,066,913 Pursuant to § 505(j)(2)(B)(iv) of the Federal Food, Drug, and Cosmetic Act. Jul. 20, 2015.

ANDA Notice Letter, Actavis Laboratories UT, Inc. to Mallinckrodt Inc. and HZNP Limited. Re: Notification of Certification for U.S. Pat. No. 9,101,591 Pursuant to § 505(j)(2)(B)(iv) of the Federal Food, Drug, and Cosmetic Act. Sep. 8, 2015.

ANDA Notice Letter, Actavis Laboratories UT, Inc. to Mallinckrodt Inc., Nuvo Research Inc. and HZNP Limited. Re: Notification of Certification for U.S. Pat. No. 9,132,110 Pursuant to § 505(j)(2)(B)(iv) of the Federal Food, Drug, and Cosmetic Act. Oct. 7, 2015.

ANDA Notice Letter, Amneal Pharmaceuticals to HZNP Limited. RE: Notice of Paragraph IV Certification of U.S. Pat. Nos. 8,217,078, 8,252,838, 8,546,450, 8,563,613, 8,618,164 8,741,956 and 8,871,809, Concerning ANDA 208198 for Diclofenac Sodium Topical Solution, 2%, Apr. 2, 2015.

ANDA Notice Letter, Amneal Pharmaceuticals to HZNP Limited RE: Notice of paragraph IV Certification of U.S. Pat. No. 9,066,913, Concerning ANDA 208198 for Diclofenac Sodium Topical Solution, 2%, Jul. 20, 2015.

ANDA Notice Letter, Amneal Pharmaceuticals to HZNP Limited. RE: Notice of Paragraph IV Certification of U.S. Pat. No. 9,101,591, Concerning ANDA 208198 for Diclofenac Sodium Topical Solution, 2%, Aug. 25, 2015.

ANDA Notice Letter, IGI Laboratories, Inc. to HZNP Limited. RE: Notice of Paragraph IV Certification of U.S. Pat. Nos. 8,217,078; 8,546,450; 8,618,164; 8,741,956; 8,252,838; 8,563,613; and 8,871,809, Concerning ANDA 208248 for Diclofenac Sodium Topical Solution, 2%, Mar. 24, 2015.

ANDA Notice Letter, IGI Laboratories, Inc. to HZNP Limited. RE: Notice of Paragraph IV Certification of U.S. Pat. No. 9,066,913, Concerning ANDA 208248 for Diclofenac Sodium Topical Solution, 2%, Jul. 29, 2015.

ANDA Notice Letter, IGI Laboratories, Inc. to HZNP Limited. Re: Notice of Paragraph IV Certification of U.S. Pat. No. 9,101,591, Concerning ANDA 208248 for Diclofenac Sodium Topical Solution, 2%, Aug. 28, 2015.

ANDA Notice Letter, IGI Laboratories, Inc. to HZNP Limited. RE: Notice of Paragraph IV Certification of U.S. Pat. Nos. 9,132,110, Concerning ANDA 208248 for Diclofenac Sodium Topical Solution, 2%, Sep. 30, 2015.

Anigbogu et al., "Fourier transform Raman spectroscopy of interactions between the penetration enhancer dimethyl sulfoxide and human stratum corneum," Int'l. J. Pharm., 1995, 125:265-282.

Baboota et al., Formulation and evaluation of once-a-day transdermal gels of diclofenac diethylamine, Methods Find. Exp. Clin. Pharmacol.. 2006, 28:109-114.

Baer et al., "Treatment of osteoarthritis of the knee with a topical diclofenac solution: a randomized controlled, 6-week trial [ISRCTN53366886]," BMC Musculoskeletal Disorders, 2005, 6:44,

(56) References Cited

OTHER PUBLICATIONS retrieved online from http://www.ncbi.nlm.nih.gov/pmc/articles/PMC 120 1146/pdf/14 71-24 74-6-44.pdf on Aug. 8, 2005.
Barry, B.W., "Mode of action of penetration enhancers in human skin," J. Controlled Release, 1987, 6:85-97.
Bayer Aspirin Label, downloaded from Drugs.com on Jan. 19, 2015.
Baynes, R.E. and Riviere, J.E., "Influence of inert ingredients in pesticide formulations on dermal absorption of carbaryl," Am. J. Vet. Res., 1998, 59:168-175.
Baynes, R.E. et al., "The influence of diethyl-m-toluamide (DEET) on the percutaneous absorption of permethrin and carbaryl," Toxicol. Appl. Pharm., 1997, 144:332-339.
Bellamy et al., "Recommendations for a core set of outcome measures for future phase III clinical trials in knee, hip, and hand osteoarthritis," J. Rheumatol., 1997, 24:799-802.
Bommannan, D., et al., J. of Controlled Release, 1991, 16, 299-304.
Bookman et al., "Effect of a topical diclofenac solution for relieving symptoms of primary osteoarthritis of the knee: a randomized controlled trial," Canadian Medical Journal, 2004, 171(4):333-338, retrieved online from http://canadianmedicaljournal.ca/cgi/reprint/171/4/333.
Boyoktimkin et al., "Chemical means of transdermal drug permeation enhancement," Chapter 11 of Transdermal and Topical Drug Delivery Systems, Tapash K. Ghosh et al., eds., 1997, pp. 357, 404-407.
Browning, R. et al., "Reducing the dose of oral NSAIDs by use of feldene gel: an open study in elderly patients with osteoarthritis," Advances in Therapy, 1994, 11(4):198-207.
Carbopol Ultrez 10 Technical Data Sheet, Jan. 2002.
Carter-Horner Corp., "Kemsol®, Dimethylsulfoxide, Scleroderma Therapy," in 2000 Compendium of Pharmaceuticals and Specialties (CPS), Louise Wellbanks et al., eds., Canadian Pharmacists Association, Ontario, Canada, 2000, p. 804.
Cevc, Gregor et al., "New, highly efficient formulation of diclofenac for the topical, transdermal administration in ultradeformable drug carriers, transfersomes," Biochimica et Biophysica Acta, Elsevier, 2001, vol. 1514, pp. 191-205.
Complaint, Horizon Pharma Ireland Limited, et al. V-Watson Laboratories, Inc., et al. U.S. District Court for the District of New Jersey. Civ. Action No. 2:14-cv-07992 (Dec. 23, 2014); Exhibit A U.S. Pat. No. 8,217,078 issued Jul. 10, 2012; Exhibit B U.S. Pat. No. 8,252,838 issued Aug. 28, 2012; Exhibit C U.S. Pat. No. 8,546,450 issued Oct. 1, 2013; Exhibit D U.S. Pat. No. 8,563,613 issued Oct. 22, 2013; Exhibit E U.S. Pat. No. 8,618,164 issued 1231-2013; Exhibit F U.S. Pat. No. 8,871,809 issued Oct. 28, 2014.
Complaint, *Horizon Pharma Ireland Limited, et al. v. Actavis Laboratories UT, Inc. et al.*, U.S. District Court for the District of New Jersey. Civ. Action No. 1:15-cv-05025 (Jun. 30, 2015); Exhibit A U.S. Pat. No. 9,066,913 issued Jun. 30, 2015; Consolidated with Civ. Action No. 2:14-cv-07992 on Jul. 16, 2015.
Complaint, *Horizon Pharma Ireland Limited, et al. v. Actavis Laboratories UT, Inc. et al.*, U.S. District Court for the District of New Jersey. Civ. Action No. To Be Assigned (Aug. 11, 2015); Exhibit A U.S. Pat. No. 9,101,591 issued Aug. 11, 2015.
Complaint, *Horizon Pharma Ireland Limited, et al. v. Actavis Laboratories UT, Inc. et al.*, U.S. District Court for the District of New Jersey. Civ. Action No. No. To Be Assigned (Sep. 17, 2015); Exhibit A U.S. Pat. No. 9,132,110 issued Sep. 15, 2015.
Complaint, *Horizon Pharma Ireland Limited, et al. v. Amneal Pharmaceuticals LLC*, U.S., Civ. Action No. No. To Be Assigned (May 15, 2015); Exhibit A U.S. Pat. No. 8,217,078 issued Jul. 10, 2012; Exhibit B U.S. Pat. No. 8,252,838 issued Aug. 28, 2012; Exhibit C U.S. Pat. No. 8,546,450 issued Oct. 1, 2013; Exhibit D U.S. Pat. No. 8,563,613 issued Oct. 22, 2013; Exhibit E U.S. Pat. No. 8,618,164 issued Dec. 31, 2013; Exhibit F U.S. Pat. No. 8,871,809 issued Oct. 28, 2014.
Complaint, *Horizon Pharma Ireland Limited, et al. v. Amneal Pharmaceuticals LLC*, U.S. District Court for the District of New Jersey. Civ. Action No. No. To Be Assigned (Jun. 30, 2015); Exhibit A U.S. Pat. No. 9,066,913 issued Jun. 30, 2015.
Complaint, *Horizon Pharma Ireland Limited, et al. v. Amneal Pharmaceuticals LLC*, U.S. District Court for the District of New Jersey. Civ. Action No. To Be Assigned (Aug. 11, 2015); Exhibit A U.S. Pat. No. 9,101,591 issued Aug. 11, 2015.
Complaint, *Horizon Pharma Ireland Limited, et al. v. Amneal Pharmaceuticals LLC*, U.S. District Court for the District of New Jersey. Civ. Action No. No. To Be Assigned (Sep. 17, 2015); Exhibit A U.S. Pat. No. 9,132,110 issued Sep. 15, 2015.
Complaint, *Horizon Pharma Ireland Limited, et al. v. IGI Laboratories Inc.*, Civ. Action No. No. To Be Assigned (May 21, 2015); Exhibit A U.S. Pat. No. 8,217,078 issued Jul. 10, 2012; Exhibit B U.S. Pat. No. 8,252,838 issued Aug. 28, 2012; Exhibit C U.S. Pat. No. 8,546,450 issued Oct. 1, 2013; Exhibit D U.S. Pat. No. 8,563,613 issued Oct. 22, 2013; Exhibit E U.S. Pat. No. 8,618,164 issued Dec. 31, 2013; Exhibit F U.S. Pat. No. 8,871,809 issued Oct. 28, 2014.
Complaint, *Horizon Pharma Ireland Limited, et al. v. IGI Laboratories, Inc., et al.* U.S. District Court for the District of New Jersey. Civ. Action No. 1:15-cv-05022 (Jun. 30, 2015); Exhibit A U.S. Pat. No. 9,066,913 issued Jun. 30, 2015.
Complaint, *Horizon Pharma Ireland Limited, et al. v. IGI Laboratories, Inc.*, U.S. District Court for the District of New Jersey. Civ. Action No. To Be Assigned (Aug. 11, 2015); Exhibit A U.S. Pat. No. 9,101,591 issued Aug. 11, 2015.
Complaint, *Horizon Pharma Ireland Limited, et al. v. IGI Laboratories, Inc.*, U.S. District Court for the District of New Jersey. Civ. Action No. To Be Assigned (Aug. 11, 2015); Exhibit A U.S. Pat. No. 9,132,110 issued Sep. 15, 2015.
Complaint, *Horizon Pharma Ireland Limited, et al. v- Paddock Laboratories, LLC, et al.* U.S. District Court for the District of New Jersey. Civ. Action No. 1:15-cv-00368 (Jan. 13, 2015); Exhibit A U.S. Pat. No. 8,217,078 issued Jul. 10, 2012; Exhibit B U.S. Pat. No. 8,252,838 issued Aug. 28, 2012; Exhibit C U.S. Pat. No. 8,546,450 issued Oct. 1, 2013; Exhibit D U.S. Pat. No. 8,563,613 issued Oct. 22, 2013; Exhibit E U.S. Pat. No. 8,618,164 issued Dec. 31, 2013; Exhibit F U.S. Pat. No. 8,871,809 issued Oct. 28, 2014.
Complaint, *Horizon Pharma Ireland Limited, et al. v- Paddock Laboratories, LLC, et al.* U.S. District Court for the District of Delaware. Civ. Action No. 1:15-cv-00043 (Jan. 14, 2015); Exhibit A U.S. Pat. No. 8,217,078 issued Jul. 10, 2012; Exhibit B U.S. Pat. No. 8,252,838 issued Aug. 28, 2012; Exhibit C U.S. Pat. No. 8,546,450 issued Oct. 1, 2013; Exhibit D U.S. Pat. No. 8,563,613 issued Oct. 22, 2013; Exhibit E U.S. Pat. No. 8,618,164 issued Dec. 31, 2013; Exhibit F U.S. Pat. No. 8,871,809 issued Oct. 28, 2014.
Complaint, *Horizon Pharma Ireland Limited, et al. v. Taro Pharmaceuticals USA, Inc. et al.*, Civ. Action No. 1:15-cv-02046 (Mar. 13, 2015); Exhibit A U.S. Pat. No. 8,217,078 issued Jul. 10, 2012; Exhibit B U.S. Pat. No. 8,252,838 issued Aug. 28, 2012; Exhibit C U.S. Pat. No. 8,546,450 issued Oct. 1, 2013; Exhibit D U.S. Pat. No. 8,563,613 issued Oct. 22, 2013; Exhibit E U.S. Pat. No. 8,618, 164 issued Dec. 31, 2013; Exhibit F U.S. Pat. No. 8,871,809 issued Oct. 28, 2014.
Complaint, *Horizon Pharma Ireland Limited, et al. v. Taro Pharmaceuticals USA, Inc. et al.* U.S. District Court for the District of New Jersey. Civ. Action No. 1:15-cv-05021 (Jun. 30, 2015); Exhibit A U.S. Pat. No. 9,066,913 issued Jun. 30, 2015.
Complaint, *Horizon Pharma Ireland Limited, et al. v. Taro Pharmaceuticals USA, Inc. et al.* U.S. District Court for the District of New Jersey. Civ. Action No. To Be Assigned (Aug. 11, 2015); Exhibit A U.S. Pat. No. 9,101,591 issued Aug. 11, 2015.
Complaint, *Horizon Pharma Ireland Limited, et al. v. Lupin Limited, et al.*, Civ. Action No. 1:15-cv-03051 (Apr. 30, 2015); Exhibit A U.S. Pat. No. 8,217,078 issued Jul. 10, 2012; Exhibit B U.S. Pat. No. 8,252,838 issued Aug. 28, 2012; Exhibit C U.S. Pat. No. 8,546,450 issued Oct. 1, 2013; Exhibit D U.S. Pat. No. 8,563,613 issued Oct. 22, 2013; Exhibit E U.S. Pat. No. 8,618,164 issued Dec. 31, 2013; Exhibit F U.S. Pat. No. 8,871,809 issued Oct. 28, 2014.
Amended Complaint, *Horizon Pharma Ireland Limited, et al. v. Lupin Limited, et al.*, U.S. District Court for the District of New Jersey, Civ. Action No. 1:15-cv-05027 (Aug. 11, 2015); Exhibit A U.S. Pat. No. 9,066,913 issued Jun. 30, 2015; Exhibit B U.S. Pat. No. 9,101,591 issued Aug. 11, 2015.

(56) References Cited

OTHER PUBLICATIONS

Complaint, *Horizon Pharma Ireland Limited, et al.* v. *Lupin Limited, et al.*, U.S. District Court for the District of New Jersey, Civ. Action No. 1:15-cv-05027 (Aug. 11, 2015); Exhibit A U.S. Pat. No. 9,066,913 issued Jun. 30, 2015.
Complaint, *Horizon Pharma Ireland Limited, et al* v. *Lupin Limited, et al.*, District Court for the District of New Jersey. Civ. Action No. No. To Be Assigned (Sep. 17, 2015); Exhibit A U.S. Pat. No. 9,132,110 issued Sep. 15, 2015.
Dachir, S., et al., "Amelioration of Sulfur Mustard Skin Injury Following a Topical Treatment with a Mixture of a Steroid and a NSAID,"J. of App. Toxicology, 2004, 24, 107-113.
Denoble, "Enhanced skin permeability by ethanol: Mechanistic studies of human stratum corneum measured by DSC and FTIR,"Pharmaceutical *Research*, vol. 4(2), p. S-59 (Apr. 1987 (Supplement)).
Dimethaid Research Inc. 2004 Annual Report (Aug. 26, 2004).
Dimethaid Research Inc. 2005 Annual Report (Aug. 29, 2005).
Dimethaid Research Inc. Press Release Entitled "Dimethaid Develops "PENNSAID® PLUS": An Innovative New Formulation for PENNSAID®" (Jul. 7, 2005).
Drug and Therapeutic Information, Inc., "A further warning on DMSO," The Medical Letter on Drugs and Therapeutics, 1965, vol. 7, No. 20, Issue 175, p. 80.
Drug and Therapeutic Information, Inc., "Dimethyl Sulfoxide (DMSO)," The Medical Letter on Drugs and Therapeutics, 1965, vol. 7, No. 11, Issue 166, pp. 42-44.
Dua, K. et al., "Formulation and evaluation of topical bases of aceclofenac," The Indian Pharmacist, Prabha Schroff, 2006, 5(45):73-75.
FDA's guidelines for inactive ingredients for Jan. 2010, 1 page, 2010.
FDA's guidelines for inactive ingredients for Jun. 2010, 1 page, 2010.
Fluhr, J.W. et al., "Transepidermal water loss reflects permeability barrier status: validation in human and rodent in vivo and ex vivo models," Exper. Derm., 2006, 15:483-492.
Franz, "Percutaneous absorption: on the Relevance of in Vitro Data," J. Invest. Derm., 1975, 64:190-195.
G.D. Searle & Co., CELEBREX® (Celecoxib) Capsules I Safety Information, Revised label based on FDA letter Feb. 23, 2000, 21 pages, G.D. Searle & Co, IL, USA and Pfizer Inc., NY, USA, Apr. 24, 2000.
G.D. Searle & Co., CELEBREX® (Celecoxib) Capsules, NOA 20-998/S-018, NOA 20-998/S-019, Revised: Jul. 2005, 25 pages (pp. 3-27), G.D. Searle LLC, Division of Pfizer Inc., NY, USA, 2005.
Galer et al., "Use of topiceuticals (topically applied, peripherally acting drugs) in the treatment of chronic pain," Curr. Drug Ther., 2006, 1(3):273-282.
Goh, C.F. et al. "Formulation of diclofenac for dermal delivery," International Journal of Pharmaceutics, 2014, 473, 607-616.
Greve, T.M. et al., "Penetration mechanism of dimethyl sulfoxide in human and pig ear skin: An ATR-FTIR and near-FT Raman spectroscopic in vivo and in vitro study," Spectroscopy, 2008, 22:405-417.
Hadgraft, J., "Mini review: Passive enhancement strategies in topical and transdermal drug delivery," Int'l. J. Pharmac., 1999, 184:1-6.
Henderson, T.R. and Henderson, R.F., "Effects of dimethyl sulfoxide on subunit proteins," Ann. N Y Acad. Sci., 1975, 243:38-53.
Hewitt, P.G., et al., "In Vitro Cutaneous Disposition of a Topical Diclofenac Lotion in Human Skin: Effect of a Multi-Dose Regimen," Pharm. Res., 1998, 15(7), 988-992.
Heyneman, C.A., et al., "Oral versus Topical NSAIDs in Rheumatic Diseases," Drugs, 2000, 60(3), 555-574.
Ho, H.-O, et al., "The Influence of Cosolvents on the In-vitro Percutaneous Penetration of Diclofenac Sodium From a Gel System," J. Pharm. Pharmacol., 1994, 46, 636-642.
Hoover, J.E. editor, *Dispensing of Medication: A Practical Manual on the Formulation and Dispensing of Pharmaceutical Products*. vol. 789. Mack Publishing Company, 1976. p. 147-8.
Hsu, L.R. et al., "The effect of pretreatment by penetration enhancers on the in vivo percutaneous absorption of piroxicam from its gel form in rabbits," Int'l. J. Pharm., 1991, 71:193-200.

Hui, X., et al., "In Vivo Bioavailability and Metabolism of Topical Diclofenac Lotion in Human Volunteers," Pharm. Res. 1998, 15(10), 1589-1595.
ICIS News, 1999-2011, http://www.chemindustry.com/chemicals/0197997.html).
Kai, T., et al., "Mechanism of percutaneous penetration enhancement: effect of n-alkanols on the permeability barrier of hairless mouse skin," J. of Controlled Release, 1990, 12, 103-112.
Kanikkannan, N. et al., "Structure-activity relationship of chemical penetration enhancers in transdermal drug delivery," Curr. Med. Chem., 1999, 6(7):593-608.
Kantarc I et al., "In vitro permeation of diclofenac sodium from novel microemulsion formulations through rabbit skin," Drug Development Research, 2005, 65:17-25.
Karande, P., "High throughput screening of transdermal formulations," Pharm. Res., 2002, 19(5):655-660.
Karande, P., "Insights into synergistic interactions in binary mixtures of chemical permeation enhancers for transdermal drug delivery," J. Controlled Release, 2006, 115:85-93.
Kemppainen, B.W. et al., "Comparison of penetration and metabolism of [3H]Diacetoxyscirpenol, [3H]Verrucarin A and [3H]T-2 toxin in skin," Fd Chem. Toxic., 1987, 25(5):379-386.
Kemppainen, B.W. et al., "Evaluation of monkey skin as a model for in vitro percutaneous penetration and metabolism of [3H]T-2 Toxin in Human Skin," Fundamental and Applied Toxicology, 1986, 7:367-375.
Kemppainen, B.W. et al., "In vitro percutaneous penetration and metabolism of [3h]t-2 toxin: comparison of human, rabbit, guinea pig and rat," Toxicon, 1987, 25(2):185-194.
Kligman, A.M., "Topical pharmacology and toxicology of dimethyl sulfoxide-Part 1," JAMA, 1965, 193(10):140-148.
Laba, "Chapter 4. Rheological Additives. Rheological Properties of Cosmetics and Toiletries," Cosmetic Science and Technology Series, 1993, vol. 13, pp. 55-152.
Lin et ai., "Efficacy of topical non-steroidal anti-inflammatory drugs in the treatment of osteoarthritis: meta-analysis of randomized controlled trials," BMJ, 2004, 329-7461, ff.
Lin, S.Y., "Direct or indirect skin lipid-ordering effect of pyrrolidone carboxylate sodium after topical treatment with penetration enhancers," Bio-Medical Materials and Engineering, 1995, 5(1):9-20.
London Gazette, Oct. 31, 1997 Issue 54935, pp. 12265-12266.
Malten, K.E. and Arend, J.D., "Topical toxicity of various concentrations of DMSO recorded with impedance measurements and water vapour loss measurements," Contact Dermatitis, 1978, 4:80-92.
Mathur et al., 2005, "Comparison of the Efficacy and Safety of Rumalaya Gel With Diclofenac Sodium Gel in the Management of Various Soft Tissue Injuries and Inflammatory Musculoskeletal Disorders," Medicine Update, 12:47-54.
McEwan, L.E., et al., "Topical diclofenac/hyaluronic acid gel in the treatment of solar keratoses," Aus. J. of Dermatology, 1997, 58, 187-189.
Mehta, Inet Continuing Education, 'Topical and Transdermal Drug Delivery: What a Pharmacist Needs to Know'; pp. 1-10, publication Sep. 2004.
Miao, Y., et al., "Preparation and Clinical Application of Diclofenac Sodium Gel," Railway Medical Journal, 2000, 28(1), 14-15.
Minghetti et al., "Ex vivo study of transdermal permeation of four diclofenac salts from different vehicles," J. of Pharm. Sci., 2007, 96(4).
Moen, "Topical diclofenac solution," Drugs, 2009, 69(18):2621-32. Retrieved online from http://www.ncbi.nlm.nih.gov/pubmed/19943711.
Morison, W.L., "Photosensitivity," N. Engl. J. Med., 2004, 350, 1111-1117.
Naito et al., "Percutaneous absorption of diclofenac sodium ointment," Int. J. Pharm., 1985, 24:115-124.
Nelson et al., "Phase IV, open-label assessment of the treatment of actinic keratosis with 3.0% diclofenac sodium topical gel (Solaraze™)," J. Drugs Derm., 2004, 3(4):401 ff.
Nishihata, T., et al., "Percutaneous absorption of diclofenac in rats and humans: aqueous gel formulation," Int. J. of Pharmaceutics, 1988, 46, 1-7.

(56) References Cited

OTHER PUBLICATIONS

Notman, R. et al., "The permeability enhancing mechanism of DMSO in ceramide bilayers simulated by molecular dynamics," Biophys. J., 2007, 93:2056-2068.
Novartis Consumer Health, Inc., Prescribing Information of Voltaren® Gel; pp. 1-23; revised Jul. 2009.
Nuvo Research Inc. Annual Report 2006.
Obata, Y., et al., "Effect of ethanol on skin permeation of nonionized and ionized diclofenac," Int. J. of Pharmaceutics, 1993, 89, 191-198.
Oertel, R.P., "Protein conformational changes induced in human stratum corneum by organic sulfoxides: An infrared spectroscopic investigation," Biopolymers, 1977, 16:2329-2345.
Ortonne, J.-P., et al., "3% diclofenac in 2.5% hyaluronic acid (Solaraze™) does not induce photosensitivity or phototoxicity alone or in combination with sunscreens," Eur. J. Dermatol., 2006, 16(4), 385-390.
Ostrenga et al., "Significance of vehicle composition I: Relationship between topical vehicle composition, skin penetrability, and clinical efficacy," J. Pharm. Sciences, 1971, 60(8).
Ott, et al., *Exposure Analysis*, CRC Press, p. 271, 2006.
Ozguney, I., "An alternative topical treatment of osteoarthritis of the knee with cutaneous diclofenac solution," Expert Opin. Pharmacother., 2008, 9(10), 1805-1816.
Pennsaid Product Monograph, 1.5% w/w diclofenac sodium solution, Date of revision: Oct. 20, 2003.
Pharmacia, Product Label: Rogaine® Extra Strength Topical Solution, Pharmacia Consumer Healthcare, Peapack, NJ, USA, 2002.
Physicians Total Care, Inc., Retin-A—tretinoin cream/tretinoin gel product insert, 6 pages, Ortho Dermatological, Division of Ortho-McNeil Pharmaceutical, Inc., Skillman, New Jersey, USA, 2001.
Pont, A.R., et al., "Effects of active sunscreen ingredient combinations on the topical penetration of the herbicide 2,4-dichlorophenoxyacetic acid," Toxicology and Industrial Health, 2003, 19, 1-8.
Popovich et al., Remington: The Science and Practice of Pharmacy, 2005, Lippincott, Williams & Wilkins, 21st Ed., p. 2033.
Prausnitz et al., "Current status and future potential of transdermal drug delivery," Nature Reviews, 2004, 3:115-124.
Retin-A Prescribing Information, Downloaded from Drugs.com on Jan. 19, 2015.
Rodgers, K. and Xiong, S., "Effect of acute administration of malathion by oral and dermal routes on serum histamine levels," Int. J. Immunopharmac., 1997, 19(8):437-441.
Rosenstein, "Topical agents in the treatment of rheumatic disorders," Rheum. Dis. Clin. North Am., 1999, 25(4):899-918.
Roth, S.H., et al., "Efficacy and Safety of a Topical Diclofenac Solution (Pennsaid) in the Treatment of Primary Osteoarthritis of the Knee," Arch. Intern. Med. 2004, 164, 2017-2023.
Sarigullu et al., "Transdermal delivery of diclofenac sodium through rat skin from various formulations," APS PharmSciTech, 2006, 7(4) Article 88 E1-E7.
Shainhouse et al., "A long-term, open-label study to confirm the safety of topical diclofenac solution containing dimethyl sulfoxide in the treatment of the osteoarthritic knee," Am. J. Therap., 2010, 0, 000-000.
Shainhouse, "OARS! guidelines for hip and knee OA: deciphering the topical drug melange," Osteoarthritis Cartilage, 2008, 16(12):1586-7.

Simon et al., "Efficacy and safety of topical diclofenac containing dimethyl sufoxide (DMSO) compared with those of topical placebo, DMSO, vehicle and oral diclofenac for knee osteoarthritis," Pain, 2009, 143(3):238-45.
Towheed, T.E., "Pennsaid® Therapy for Osteoarthritis of the Knee: A Systematic Review and Metaanalysis of Randomized Controlled Trials," Journal of Rheumatology, 2006, 33(3), 567-573.
Towheed, "Published meta-analyses of pharmacological therapies for osteoarthritis," Osteoarthritis and Cartilage, 2002, 10:836-837.
Tugwell, P.S., et al., "Equivalence Study of a Topical Diclofenac Solution (Pennsaid®) Compared with Oral Diclofenac in Symptomatic Treatment of Osteoarthritis of the Knee: A Randomized Controlled Trial," Journal of Rheumatolonv, 2004, 31(10), 2002-2012.
Vivian, J.C., et al., "Remington: The Science and Practice of Pharmacy, 21st ed." 2005, p. 2015-2054.
Walker, R.B. and Smith E.W., "The role of percutaneous penetration enhancers," Advanced Drug Delivery Reviews, 1996, 18:295-301.
Waller, J.M. et al., "'Keratolytic' properties of benzoyl peroxide and retinoic acid resemble salicylic acid in man," Skin Pharmacol. Physiol., 2006, 19:283-289.
Williams, A.G., et al., "Penetration enhancers," Adv. Drug. Deliv. Rev. 2004, 56, 603-618.
Wolf, J.E. Jr., et al. "Topical 3.0% diclofenac in 2.5% hyaluronan gel in the treatment of actinic keratosis," Int. J. Dermatology, 2001, 40, 709-713.
ANDA Notice Letter, Amneal Pharmaceuticals to HZNP Limited. RE: Notice of Paragraph IV Certification of U.S. Pat. Nos. 9,168,304 and 9,168,305, Concerning ANDA 208198 for Diclofenac Sodium Topical Solution, 2%, Nov. 10, 2015.
ANDA Notice Letter, Paddock Laboratories, LLC to Mallinckrodt Inc. and HZNP Limited. Re: Notification of Certification of Invalidity, Unenforceability, and/or NonInfringement for U.S. Pat. Nos. 9,168,304 and 9,168,305, Pursuant to § 505(j)(2)(B)(iv) of the Federal Food, Drug, and Cosmetic Act. Nov. 10, 2015.
ANDA Notice Letter, Teligent Inc. (formerly IGI) Re: Abbreviated New Drug Application 208428 Diclofenac Topical Solution 2% and Offer of Confidential Access; Paragraph IV Certification of U.S. Pat. Nos. 9,168,304 and 9,168,305, Dec. 3, 2015.
Complaint, *Horizon Pharma Ireland Limited, et al.* v. *Actavis Laboratories UT, Inc. et al.*, U.S. District Court for the District of New Jersey, Civ. Action No. 1:15-cv-07742 (Oct. 27, 2015); Exhibit A U.S. Pat. No. 9,168,304 issued Oct. 27, 2015; Exhibit B U.S. Pat. No. 9,168,305 issued Oct. 27, 2015.
Complaint, *Horizon Pharma Ireland Limited, et al.* v. *Amnea Pharmaceuticals LLC*, U.S. District Court for the District of New Jersey, Civ. Action No. 1:15-cv-07743 (Oct. 27, 2015); Exhibit A U.S. Pat. No. 9,168,304 issued Oct. 27, 2015; Exhibit B U.S. Pat. No. 9,168,305 issued Oct. 27, 2015.
Complaint, *Horizon Pharma Ireland Limited, et al.* v. *IGI Laboratories, Inc.*, U.S. District Court for the District of New Jersey, Civ. Action No. 1:15-cv-07744 (Oct. 27, 2015); Exhibit A U.S. Pat. No. 9,168,304 issued Oct. 27, 2015; Exhibit B U.S. Pat. No. 9,168,305 issued Oct. 27, 2015.
Complaint, *Horizon Pharma Ireland Limited, et al.* v. *Lupin Limited, et al.*, U.S. District Court for the District of New Jersey, Civ. Action No. 1:15-cv-07745 (Oct. 27, 2015); Exhibit A U.S. Pat. No. 9,168,304 issued Oct. 27, 2015; Exhibit B U.S. Pat. No. 9,168,305 issued Oct. 27, 2015.

DICLOFENAC TOPICAL FORMULATION

CROSS-REFERENCES TO RELATED APPLICATIONS

This application is a continuation of U.S. application Ser. No. 14/705,649, filed May 6, 2015, which application is a continuation of U.S. application Ser. No. 14/497,096, filed Sep. 25, 2014, now U.S. Pat. No. 9,066,913, which application is a continuation of U.S. application Ser. No. 14/025,781, filed Sep. 12, 2013, now U.S. Pat. No. 8,871,809, which application is a continuation of U.S. application ser. No. 13/564,688, filed Aug. 1, 2012, now U.S. Pat. No. 8,563,613, which application is a continuation of U.S. application Ser. No. 12/134,121, filed Jun. 5, 2008, now U.S. Pat. No. 8,252,838, which application is a continuation of PCT/US2007/081674, filed Oct. 17, 2007, which application claims priority to U.S. Provisional Application No. 60/829,756, filed Oct. 17, 2006, the teachings all of which are incorporated herein by reference in their entireties for all purposes.

FIELD OF THE INVENTION

The present invention relates generally to compositions and methods for treating osteoarthritis.

BACKGROUND OF THE INVENTION

1. Osteoarthritis

Osteoarthritis (OA) is a chronic joint disease characterized by progressive degeneration of articular cartilage. Symptoms include joint pain and impaired movement. OA is one of the leading causes of disability worldwide and a major financial burden to health care systems. It is estimated to affect over 15 million adults in the United States alone. See Boh L. E. Osteoarthritis. In: DiPiro J. T., Talbert R. L., Yee G. C., et al., editors. *Pharmacotherapy: a pathophysiological approach.* 4th ed. Norwalk (CT): Appleton & Lange, pp. 1441-59 (1999).

Oral non-steroidal anti-inflammatory drugs (NSAIDs) are a mainstay in the management of OA. They have analgesic, anti-inflammatory and antipyretic effects and are useful in reducing pain and inflammation. NSAIDS are however associated with serious potential side effects including nausea, vomiting, peptic ulcer disease, GI haemorrhage, and cardiovascular events.

Topical NSAIDs offer the possibility of achieving local therapeutic benefit while reducing or eliminating the risk of systemic side effects. There has been widespread interest in this approach to treating OA, but data in support of the efficacy of topical NSAIDs in the treatment of OA is limited. For instance, a study of 13 randomized placebo controlled trials (RCT's) of various topical NSAIDs tested specifically for use in the treatment of OA concluded that they were not generally efficacious for chronic use in OA. (Lin et al., Efficacy of topical non-steroidal anti-inflammatory drugs in the treatment of osteoarthritis: meta-analysis of randomized controlled trials, *BMJ*, doi:10.1136/bmj.38159.639028.7C (2004)).

There are generally three outcomes used to measure the efficacy of an OA treatment: pain, physical function, and a patient global assessment. See Bellamy N., Kirwan J., Boers M., Brooks P., Strand V., Tugwell P., et al. Recommendations for a core set of outcome measures for future phase III clinical trials in knee, hip and hand osteoarthritis. Consensus development at OMERACT III., *J Rheumatol,* 24:799-802 (1997). To be suitable for chronic use, a therapy must generally show efficacy on these three variables over a sustained period of time. In the U.S. for instance, the Food and Drug Administration (FDA) requires OA therapies to show superiority over placebo over a 12 week period. Notwithstanding the significant potential for topical NSAIDs in the treatment of OA, as of the time of filing this application, none have been approved for such treatment in the U.S.

U.S. Pat. Nos. 4,575,515 and 4,652,557 disclose topical NSAID compositions, one of which, consisting of 1.5% diclofenac sodium, 45.5% dimethylsulphoxide, 11.79% ethanol, 11.2% propylene glycol, 11.2% glycerine, and water, has been shown to be effective in chronic OA treatment. See Towheed, *Journal of Rheumatology* 33:3 567-573 (2006) and also Oregon Evidence Based Practice Center entitled "Comparative Safety and Effectiveness of Analgesics for Osteoarthritis", AHRQ Pub. No. 06-EHC009-EF. This particular composition is referred to herein as "comparative liquid formulation" or "comparative" in the Examples section. However, the compositions of these prior inventions have drawbacks in that they are slow to dry and runny. They also require frequent dosing of three to four times a day to achieve efficacy in OA, which increases exposure to potential skin irritants and increases the risk of skin irritation.

In general, the failure of topical NSAIDs to fulfill their promise in OA may be due in part to the difficulty associated with delivering a molecule through the skin in sufficient quantities to exert a therapeutic effect and in a manner that makes the treatment itself tolerable. It is generally believed that clinical efficacy in OA requires absorption of the active ingredient and its penetration in sufficient quantities into underlying inflamed tissues including the synovium and synovial fluid of joints. See Rosenstein, Topical agents in the treatment of rheumatic disorders, *Rheum. Dis. Clin North Am.*, 25: 899-918 (1999).

However, the skin is a significant barrier to drug permeation, and despite nearly four decades of extensive research, the success of transdermal drug delivery in general remains fairly limited with only a small number of transdermal drug products commercially available.

In connection with topical dosage forms applied to the skin, a number of interactions can occur including vehicle-skin, vehicle-drug, and drug-skin. Each can affect the release of an active agent from a topical dosage form (Roberts, M. S.: Structure-permeability considerations in percutaneous absorption. In *Prediction of Percutaneous Penetration*, ed. by R. C. Scott et al., vol. 2, pp.210-228, IBC Technical Services, London, 1991). Thus various factors can affect absorption rates and penetration depth including the active ingredient, the vehicle, the pH, and the relative solubility of the active in the vehicle versus the skin (Ostrenga J. et al., Significance of vehicle composition I: relationship between topical vehicle composition, skin penetrability, and clinical efficacy, *Journal of Pharmaceutical Sciences,* 60: 1175-1179 (1971)). More specifically, drug attributes such as solubility, size and charge, as well as, vehicle attributes such as the drug dissolution rate, spreading-ability, adhesion, and ability to alter membrane permeability can have significant effects on permeability.

There is significant variability observed from seemingly minor variations in formulations. For instance, Naito demonstrates significant variability in penetration among topical NSAID formulations simply by changing the gelling agent used in the compositions (Naito et al., Percutaneous absorption of diclofenac sodium ointment, *Int. Jour. of Pharmaceutics,* 24: 115-124 (1985)). Similarly, Ho noted significant variability in penetration by changing the proportions of alcohol, propylene glycol, and water (Ho et al., The influence of cosolvents on the in-vitro percutaneous penetration of diclofenac sodium from a gel system, *J Pharm. Pharmacol.*, 46:636-642 (1994)). It was noted that the changes affected three distinct variables: (i) the solubility of the drug in the vehicle, (ii) the partition coefficient, and (iii) effects on alteration of skin structure.

Ho et al. (1994) also noted that (i) the pH of the vehicle, (ii) the drug solubility, and (iii) the viscosity of a gel matrix can influence penetration from a gel dosage form. The pH value affects the balance between ionized and non-ionized forms of the drug, which have different penetration properties (Obata, *International Journal of Pharmaceutics*, 89: 191-198 (1993)). The viscosity can affect diffusion of the drug through the gel matrix and release of the drug from the vehicle into the skin. The solubility of the drug in the vehicle will affect the partition coefficient of the drug between the formulation and the recipient membrane/tissue (Ho et al. 1994).

Chemical penetration enhancers are one means for reversibly lowering the skin barrier. Other methods include iontophoresis, ultrasound, electroporation, heat, and microneedles. At least 250 chemicals have been identified as enhancers that can increase skin permeability. General categories include pyrrolidones, fatty acids, esters and alcohols, sulfoxides, essential oils, terpenes, oxazoldines, surfactants, polyols, azone and derivatives, and epidermal enzymes.

The mechanisms by which penetration enhancers reduce the skin barrier function are not well understood (see Williams and Barry "Penetration Enhancers" *Advanced Drug Delivery Reviews* 56: 603-618 (2004)) although it has been proposed that the mechanisms can be grouped into three broad categories: lipid disruption, increasing corneocyte permeability, and promoting partitioning of the drug into the tissue.

The challenge with use of chemical penetration enhancers is that few seem to induce a significant or therapeutic enhancement of drug transport at tolerable levels. This is because the act of disrupting the skin barrier will have the potential of causing skin irritation. With increased disruption, skin irritation will become a greater issue. This is particularly problematic with topical OA treatments where the goal is to have the active penetrate into joint tissue and where the drug must be utilized on a long-term basis due to the nature of the disease. The inventors have developed methods and compositions that deliver more active ingredient per unit dose than previously known compositions, and this would be expected to lead to a lower incidence of skin irritation.

The compositions of the invention use diclofenac sodium which is a commonly used NSAID. Diclofenac has four different salts that show significant variability in the degree of permeation in solutions using different solvents. Minghetti, for instance, teaches that a diclofenac salt with an organic base is best for topical applications (Minghetti et al., Ex vivo study of trandermal permeation of four diclofenac salts from different vehicles, *Jour. of Pharm. Sci*, DOI 10.1002/jps.20770 (2007)).

Other research points to microemulsion formulations as a means for delivery of diclofenac sodium (Kantarci et al., In vitro permeation of diclofenac sodium from novel microemulsion formulations through rabbit skin, *Drug Development Research*, 65:17-25 (2005); and Sarigullu I. et al., Transdermal delivery of diclofenac sodium through rat skin from various formulations, *APS PharmSciTech*, 7(4) Article 88, E1-E7 (2006)).

Other topical diclofenac compositions are disclosed in a number of patents including U.S. Pat. Nos. 4,543,251, 4,670,254, 5,374,661, 5,738,869, 6,399,093 and 6,004,566. United States Patent Application No. 20050158348 points out that various solvents are widely used for gel preparations, but notes that they are limited in potential due to skin irritation. This reference also notes that gel compositions are associated with fast termination of action as the active precipitates from solution in the upper skin layers, limiting anti-inflammatory action in deeper tissues. The gels of the present invention are designed to accomplish the opposite, namely prolonged action and anti-inflammatory action in the deeper tissues.

2. Gel Formulations of Diclofenac

None of the previous references disclose the compositions of the invention or their use in the treatment of OA. Rather, these references highlight the significant unmet need with respect to topical OA treatments for chronic use and the complexity of transdermal transport in general where significant variability in permeation is observed by changing composition elements or their relative proportions.

In light of the foregoing, there is a considerable need for improvement in the development of a topical NSAID suitable for long term use in the treatment of OA. The challenge has been to develop an optimal formulation which will deliver the active agent to the underlying tissue in sufficient concentration to treat OA on a long term basis, while reducing or minimizing the incidence of intolerable skin irritation caused by disrupting the skin barrier and while providing a formulation and dosage that leads to and encourages patient compliance. The present invention satisfies these and other needs.

BRIEF SUMMARY OF THE INVENTION

The present invention overcomes the disadvantages of the prior art by providing diclofenac sodium gel formulations for the treatment of osteoarthritis that display a better drying time, higher viscosity, increased transdermal flux, and greater pharmacokinetic absorption in vivo when compared to previously described compositions. Furthermore, the preferred diclofenac sodium gel formulations of the present invention provide other advantages including favorable stability at six (6) months as reflected in the lack of any substantial changes in viscosity, the absence of phase separation and crystallization at low temperatures, and a low level of impurities. Moreover, the present gel formulations adhere well to the skin, spread easily, dry quicker, and show greater in vivo absorption in comparison to previously described compositions. Thus, the gel formulations of the present invention provide superior means for delivery of diclofenac sodium through the skin for the treatment of osteoarthritis, as compared to previously described formulations.

As such, in one embodiment, the present invention provides a gel formulation comprising, consisting essentially of, or consisting of:
 (i) diclofenac sodium;
 (ii) DMSO;
 (ii) ethanol;
 (iii) propylene glycol;
 (v) a thickening agent;
 (vi) optionally glycerol; and
 (vii) water.

In another embodiment, the present invention provides a method of treating osteoarthritis in a subject suffering from articular pain, the method comprising the topical administration to an afflicted joint area of a subject a therapeutically effective amount of a gel formulation comprising, consisting essentially of, or consisting of:
 (i) diclofenac sodium;
 (ii) DMSO;
 (ii) ethanol;
 (iii) propylene glycol;
 (v) a thickening agent;

(vi) optionally glycerol; and
(vi) water,
thereby treating osteoarthritis.

A further embodiment provides for the use of diclofenac sodium in the preparation of a medicament for the treatment of pain, the medicament comprising a gel formulation comprising, consisting essentially of, or consisting of:
(i) diclofenac sodium;
(ii) DMSO;
(ii) ethanol;
(iii) propylene glycol;
(v) a thickening agent;
(vi) optionally glycerol; and
(vii) water.

In yet a further embodiment, the present invention provides a gel formulation comprising, consisting essentially of, or consisting of: a diclofenac sodium solution and at least one thickening agent, which can be selected from cellulose polymer, a carbomer polymer, a carbomer derivative, a cellulose derivative, polyvinyl alcohol, poloxamers, polysaccharides, and mixtures thereof.

In an aspect of this embodiment, the diclofenac sodium solution comprises, consists essentially of, or consists of:
(i) diclofenac sodium;
(ii) DMSO;
(ii) ethanol;
(iii) propylene glycol;
(iv) optionally glycerol; and
(v) water.

In an aspect of the above embodiments, the thickening agents can be selected from cellulose polymers, carbomer polymers, a carbomer derivative, a cellulose derivative, polyvinyl alcohol, poloxamers, polysaccharides, and mixtures thereof.

In an aspect of the above gel embodiments, diclofenac sodium is present at 1-5% w/w, such as 1, 2, 3, 4, or 5% w/w; DMSO is present at 30-60% w/w; ethanol is present at 1-50% w/w; propylene glycol is present at 1-15% w/w; glycerol is present at 0-15% w/w, a thickening agent is present such that the end viscosity of the gel is between 10 and 50000 centipoise; and water is added to make 100% w/w. In other aspects, glycerol is present at 0-4% w/w. In further aspects, no glycerol is present.

In another aspect of the above embodiments, diclofenac sodium is present at 2% w/w; DMSO is present at 45.5% w/w; ethanol is present at 23-29% w/w; propylene glycol is present at 10-12% w/w; hydroxypropylcellulose (HY119) is present at 0-6% w/w; glycerol is present at 0-4%, and water is added to make 100% w/w. In other aspects, there is no glycerol in the gel formulation. In further aspects, the end viscosity of the gel is 500-5000 centipoise.

A feature of the above gel formulations is that when such formulations are applied to the skin, the drying rate is quicker and transdermal flux is higher than previously described compositions, such as those in U.S. Pat. Nos. 4,575,515 and 4,652,557. Additional features of the preferred formulations include decreased degradation of diclofenac sodium, which degrades by less than 0.04% over the course of 6 months and a pH of 6.0-10.0, for example around pH 9.0.

In certain embodiments, the gel formulations of the invention comprise 1-5% glycerol, wherein the gel formulation when applied to the skin has a drying rate and transdermal flux greater than a comparative liquid formulation. In some aspects, the drying rate results in a residue of at most 50% of a starting amount after 24 hours and the transdermal flux is 1.5 or more greater than a comparative liquid formulation as determined by Franz cell procedure at finite or infinite dosing or both.

In other embodiments, the gel formulations and methods of their use provide a reduction of pain over 12 weeks when the formulations are applied topically. In various aspects, the gel formulations are applied twice daily and the pain can be due to osteoarthritis.

These and other objects, embodiments, and advantages will become more apparent when read with the figures and detailed description which follow.

DETAILED DESCRIPTION OF THE INVENTION

I. Definitions

Figure 1:
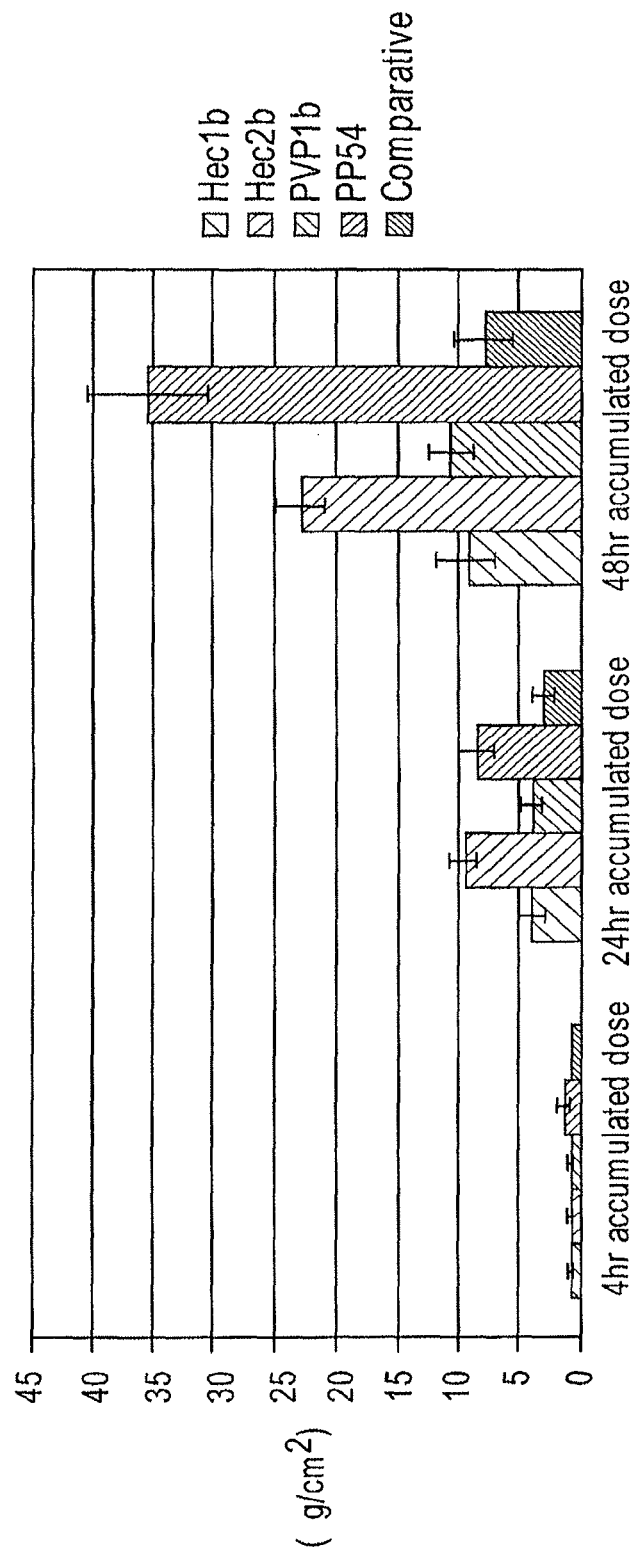
FIG. 1 shows a bar graph of flux rate of HEC and PVP gels. Franz diffusion cells were dosed at 15 mg per Franz cell.

The term "transdermal" is used herein to generally include a process that occurs through the skin. The terms "transdermal" and "percutaneous" are used interchangeably throughout this specification.

The term "topical formulation" is used herein to generally include a formulation that can be applied to skin or a mucosa. Topical formulations may, for example, be used to confer therapeutic benefit to a patient or cosmetic benefits to a consumer. Topical formulations can be used for both topical and transdermal administration of substances.

The term "topical administration" is used herein to generally include the delivery of a substance, such as a therapeutically active agent, to the skin or a localized region of the body.

The term "transdermal administration" is used herein to generally include administration through the skin. Transdermal administration is often applied where systemic delivery of an active is desired, although it may also be useful for delivering an active to tissues underlying the skin with minimal systemic absorption.

The term "penetration enhancer" is used herein to generally include an agent that improves the transport of molecules such as an active agent (e.g., a medicine) into or through the skin. Various conditions may occur at different sites in the body either in the skin or below the skin creating a need to target delivery of compounds. For example, in a treatment for osteoarthritis, the delivery of the active agent into relatively deep underlying joint tissue may be necessary to achieve therapeutic benefit. Thus, a "penetration enhancer" may be used to assist in the delivery of an active agent directly to the skin or underlying tissue or indirectly to the site of the disease through systemic distribution. A penetration enhancer may be a pure substance or may comprise a mixture of different chemical entities.

The term "finite dosing" is used herein to generally include an application of a limited reservoir of an active agent. The reservoir of the active agent is depleted with time leading to a tapering off of the active absorption rate after a maximum absorption rate is reached.

The term "infinite dosing" is used herein to generally include an application of a large reservoir of an active agent. The reservoir is not significantly depleted with time, thereby providing a long term, continuous steady state of active absorption.

As used herein, the term "comparative liquid formation" or "comparative" refers to a formulation such as that described in U.S. Pat. Nos. 4,575,515 and 4,652,557 consisting of 1.5% diclofenac sodium, 45.5% dimethylsulfoxide, 11.79% ethanol, 11.2% propylene glycol, 11.2% glycerine, and water.

II. Gel Formulations

1. Components of the Gel Formulations

In order to provide a diclofenac sodium gel formulation having improved properties of drying time, increased transdermal flux and greater pharmacokinetic absorption in vivo, higher viscosity, good adherence to the skin, and ready spreadability, while maintaining stability over time, the inventors have discovered that a surprisingly advantageous combination of the following components can be used in the preparation of the gel compositions of the present invention.

The present invention provides gel formulations comprising an active agent, preferably a non-steroidal anti-inflammatory drug or pharmaceutically acceptable salts thereof More preferably, the non-steroidal anti-inflammatory is diclofenac, which can exist in a variety of salt forms, including sodium, potassium, and diethylamine forms. In a preferred embodiment, the sodium salt of diclofenac is used. Diclofenac sodium may be present in a range of approximately 0.1% to 10%, such as 1, 2, 3, 4, or 5% w/w. Use of the sodium salt has been known to create a challenge with respect to stability of an aqueous gel in that higher salt concentrations can cause a breakdown in the gel matrix through interaction with certain thickening agents.

In another embodiment, the present invention includes a penetration enhancer. The penetration enhancer may be dimethyl sulfoxide ("DMSO") or derivatives thereof The DMSO may be present in an amount by weight of 1% to 70%, and more preferably, between 25% and 60%, such as 25, 30, 40, 45, 50, 55, or 60% w/w. Preferably, DMSO is used in the present invention at a concentration of about 40 to about 50% w/w, such as 41, 42, 43, 44, 45, 46, 47, 48, 49 and 50% and all fractions in between such as 44, 44.5, 45, 45.5, 46, 46.5%, and the like.

In certain embodiments, the present invention includes a lower alkanol, such as methanol, ethanol, propanol, butanol or mixtures thereof In certain embodiments, the alkanol is present at about 1 to about 50% w/w. Preferably, ethanol is used at about 1-50% w/w, such as 1, 5, 10, 15, 20, 25, 30, 35, 40, 45, or 50% w/w, and all fractions in between.

In certain embodiments, the present invention includes a polyhydric alcohol, such as a glycol. Suitable glycols include ethylene glycol, propylene glycol, butylene glycol, dipropylene glycol, hexanetriol and a combination thereof Preferably, propylene glycol is used at about at 1-15% w/w, such as 1, 2, 3, 4, 5, 6, 7, 8, 9, 10, 11, 12, 13, 14, or 15% w/w, and all fractions in between.

In certain embodiments, the present invention includes glycerol (also referred to herein as glycerine) at a concentration of 0-12% w/w. Preferably, glycerol is used at 0-4% w/w, such as 0, 1, 2, 3, or 4% w/w, and all fractions in between. In some embodiments, no glycerol is used in the formulation.

In a preferred embodiment, the present invention provides a formulation comprising a diclofenac solution and at least one thickening agent to make a gel. The at least one thickening agent of the present invention may be an acrylic polymer (for example, Carbopol polymers, Noveon polycarbophils and Pemulen polymeric emulsifiers available commercially from Noveon Inc. of Cleveland, Ohio), an acrylic polymer derivative, a cellulose polymer, a cellulose polymer derivative, polyvinyl alcohol, poloxamers, polysaccharides or mixtures thereof. Preferably the at least one thickening agent is hydroxypropylcellulose (HPC) used such that the end viscosity is between 10 and 50000 centipoise (cps). More preferably the end viscosity is between 500 and 20000 cps.

The present gel formulation may optionally include at least one antioxidant and/or one chelating agent.

Preferred antioxidants for use in the present invention may be selected from the group consisting of butylated hydroxytoluene (BHT), butylated hydroxyanisole (BHA), ascorbyl linoleate, ascorbyl dipalmitate, ascorbyl tocopherol maleate, calcium ascorbate, carotenoids, kojic acid, thioglycolic acid, tocopherol, tocopherol acetate, tocophereth-5, tocophereth-12, tocophereth-18, tocophereth-80, and mixtures thereof.

Preferred chelating agents may be selected from the group consisting of ethylenediamine tetraacetic acid (EDTA), diammonium EDTA, dipotassium EDTA, calcium disodium EDTA, HEDTA, TEA-EDTA, tetrasodium EDTA, tripotassium EDTA, trisodium phosphate, diammonium citrate, galactaric acid, galacturonic acid, gluconic acid, glucuronic acid, humic acid, cyclodextrin, potassium citrate, potassium EDTMP, sodium citrate, sodium EDTMP, and mixtures thereof.

In addition, the topical formulations of the present invention can also comprise a pH adjusting agent. In one particular embodiment, the pH adjusting agent is a base. Suitable pH adjusting bases include bicarbonates, carbonates, and hydroxides such as alkali or alkaline earth metal hydroxide as well as transition metal hydroxides. Alternatively, the pH adjusting agent can also be an acid, an acid salt, or mixtures thereof Further, the pH adjusting agent can also be a buffer. Suitable buffers include citrate/citric acid buffers, acetate/acetic acid buffers, phosphate/phosphoric acid buffers, formate/formic acid buffers, propionate/propionic acid buffers, lactate/lactic acid buffers, carbonate/carbonic acid buffers, ammonium/ammonia buffers, and the like. The pH adjusting agent is present in an amount sufficient to adjust the pH of the composition to between about pH 4.0 to about 10.0, more preferably about pH 7.0 to about 9.5. In certain embodiments, the unadjusted pH of the admixed components is between 8 and 10, such as 9, without the need for the addition of any pH adjusting agents.

2. Characteristics of the Gel Formulation a) Transdermal Flux

As shown below in the Examples, the present invention provides diclofenac sodium gel formulations that display surprisingly effective rates of transdermal flux when compared to previously described formulations.

Accordingly, in one embodiment, the present gel formulation comprises a non-steroidal anti-inflammatory and at least one thickening agent and having a flux, as determined by a finite dose Franz cell procedure, equal to or greater than the flux of a comparative liquid formulation. Preferably, the flux is greater than the flux of the comparative liquid formulation. More preferably, the flux is at least 1.5 times greater than the flux of the comparative liquid formulation. In other words, the ratio of: (i) the flux of the gel formulation comprising the non-steroidal anti-inflammatory and at least one thickening agent to (ii) the flux of the comparative liquid formulation is preferably greater than 1.0, and more preferably at least about 1.5.

In a further embodiment, the present invention further provides a diclofenac sodium gel formulation comprising a diclofenac solution and at least one thickening agent and having a flux as determined by the finite Franz cell procedure at least equivalent to the flux of the diclofenac solution alone. Preferably, the diclofenac sodium gel formulation has a flux that is at least 2.0 times greater compared to the flux of the diclofenac sodium solution alone. More preferably, the present invention provides a diclofenac sodium gel formulation having a flux that is at least 4.0 times greater compared to the flux of the diclofenac sodium solution alone. In other words, the ratio of: (i) the flux of the diclofenac sodium gel formulation to (ii) the flux of the diclofenac sodium solution is at least about 1.0, preferably at least about 2.0, more preferably at least about 4.0.

In a yet further embodiment, the present invention provides a diclofenac sodium gel formulation comprising diclofenac sodium and at least one thickening agent and having a flux as determined by the multiple finite dosing Franz cell procedure (dosing at 2.5mg/cm$^2$ at 0 and 6 hours) of at least 0.1 µg/hr/cm$^2$ at 24 hours, preferably at least 0.2 µg/hr/cm$^2$ at 24 hours.

b) Viscosity

In another embodiment, the present invention provides a gel formulation comprising a non-steroidal anti-inflammatory drug (NSAID) and at least one thickening agent, the gel formulation having a viscosity of at least 100 cP. Preferably, the gel formulation has a viscosity of at least 500 cP. More preferably, the gel formulation has a viscosity of at least 1000 cP. In other embodiments, the viscosity is 5000-10,000, 10,000-15,000, or 15,000-20,000 cP.

In a further embodiment, the present invention provides a diclofenac gel formulation comprising a diclofenac solution and at least one thickening agent, the gel formulation having a viscosity of around 1000 cP and a flux of at least 0.2 µg/cm$^2$/hr as determined by the multiple finite dose Franz cell procedure (2.5 mg/cm$^2$ at 0 and 6 hours) at 24 hours.

c) Stability

The stability of a drug product composition can have a significant impact on the length and cost of drug development, the nature of the studies required to support regulatory submissions, and the ultimate safety and approvability.

It is important for instance to minimize the amount of impurities or degradation products that form over time due to interactions between the various ingredients in a composition. This can be particularly important in compositions that are designed to increase skin permeability.

Thus, in some embodiments, the present invention provides a diclofenac sodium gel formulation that degrades by less than 1% over the course of 6 months at room temperature. More preferably, the rate of degradation is less than 0.9, 0.8, 0.7, 0.6, 0.5, 0.4, 0.3, 0.2, or less than 0.1%, and all fractions in between, over the course of 6 months at room temperature.

d) Drying Time

Relative to previously disclosed compositions, such as those in U.S. Pat. Nos. 4,575,515 and 4,652,557 (termed herein as "comparative liquid formulation" or "comparative"), the compositions of the invention dry quicker while achieving higher transdermal flux of the drug. It is surprising that higher flux rate and quicker drying can be achieved together as skin hydration is known to increase transdermal flux or penetration. The drying of the skin caused by rapid evaporation would tend to reduce the transdermal transport of drug remaining on the skin. The drying time difference is evident when equal amounts of the two products are tested on opposite limbs. Within thirty (30) minutes the compositions of the invention are almost completely dry whereas a significant amount of the previously described liquid formulation remains.

To compare the drying times more quantitatively, side-by-side comparisons were conducted. To accomplish this, the inventors measured the residual weight of formulations by placing equal amounts (100 mg) of a prior art formulation and compositions of the invention in weighing dishes over 10 cm$^2$ areas and weighing the amount remaining over time. Using this methodology, a difference is immediately noticeable, and becomes dramatically different by 4 hours (Table 11 and FIG. 10).

e) Pharmacokinetics

A comparison of the absorption of diclofenac sodium of compositions of the invention and a comparable composition from U.S. Pat. Nos. 4,575,515 and 4,652,557 was conducted in animals. The gels of the invention were shown to have improved absorption on a per dose basis than the comparative liquid compositions of these patents. In absolute terms, the clinical dose of the gels of the invention delivered a maximum observed plasma concentration ($C_{max}$) at steady state of 81 ng/ml and an area under the curve (AUC) of 584 ng/ml. This compared to 12 ng/ml and 106 ng/ml for the comparator compositions.

These results speak to the properties of the vehicle in delivering the active agent. The higher numbers for gel were seen even though the solution composition was dosed four (4) times per day (total 5.2 ml) compared to twice (2) per day (total 4.0 ml) for the gels.

III Preparation of Gel Formulations

In another embodiment, the present invention provides a method for making gel formulations of diclofenac sodium. The gel formulations of the present invention are preferably made by carrying out the following steps: (i) dispersing the thickener, derivative thereof and/or mixture thereof in dimethyl sulfoxide and stirring for 1 hour; (ii) dissolving diclofenac sodium in an aqueous alcohol mixture (e.g., an ethanol/water mixture); (iii) dispersing propylene glycol and glycerol into the NSAID solution from (ii); and (iv) mixing the resulting NSAID solution into the thickener/dimethyl sulfoxide blend and stirring for 1 hour at ambient temperature. Alternatively, the gel formulations of the present invention may be made by carrying out the following steps: (i) dissolving the NSAID (e.g., diclofenac sodium) in an alcohol solution of DMSO (e.g., an ethanol/dimethyl sulfoxide mixture); (ii) dispersing the thickener, derivative thereof and/or mixture thereof in a solution of water/propylene glycol/glycerol and stirring for 1 hour; (iii) mixing the NSAID solution from (i) into the thickener blend from (ii) and stirring for 1 hour at ambient temperature. Heating can also be used during these mixing processes to help facilitate the gel formation.

Diclofenac sodium may be present in a range of approximately 0.1% to 10% w/w, such as 0.5, 1.0, 1.5, 2.0, 2.5, 3.0, 3.5, 4.0, 5.0, 6.0, 7.0, 8.0, and 9.0% w/w.

IV Methods of Use

Compositions of the invention are particularly suited for use in treating osteoarthritis (OA) chronically. They may also be useful for the treatment of other chronic joint diseases characterized by joint pain, degeneration of articular cartilage, impaired movement, and stiffness. Suitable joints include the knee, elbow, hand, wrist and hip.

Due to the properties of higher flux and greater in vivo absorption, it is believed that the formulations of the present invention can be administered at lower dosing than previously described formulations. In particular, it is expected that the compositions of the invention can be used at twice a day dosing or once a day dosing in the treatment of OA. This would represent a significant improvement as lower dosing is associated with better patient compliance, an important factor in treating chronic conditions.

Suitable amounts per administration will generally depend on the size of the joint, which varies per individual and per joint, however a suitable amount may range from 0.5 µl/cm$^2$ to 4.0 µl/cm$^2$. Preferably the amount ranges from 2.0 to 3.0 µl/cm$^2$.

Compositions of the present invention may, if desired, be presented in a bottle or jar or other container approved by the FDA, which may contain one or more unit dosage forms containing the active ingredient. The pack or dispenser may also be accompanied by a notice associated with the container in a form prescribed by a governmental agency regulating the manufacture, use or sale of pharmaceuticals, which notice indicates approval by the agency of the form of the compositions for human or veterinary administration. Such notice, for example, may be of labeling approved by the U.S. Food and Drug Administration for prescription drugs, or of an approved product insert. Compositions comprising a preparation of the invention formulated in a compatible pharmaceutical carrier may also be prepared, placed in an appropriate container, and labeled for treatment of an indicated condition.

The following examples are offered to illustrate, but not to limit, the claimed invention.

V Examples

Example 1

Materials and Methods

Table 1 provides a list of the materials used in the examples provided below:

TABLE 1

Materials

| Abbr | Chemical | FW | Source | Vendor # | CAS |
|---|---|---|---|---|---|
| BHA | Butylated hydroxyanisole | 180.24 | Sigma | B1253 | 25013-16-5 |
| BHT | Butylated hydroxytoluene | 220.36 | Spectrum | BH110-07 | 128-37-0 |
| Carb940 | Carbopol 940 | | Noveon | Carbopol 940 | 9003-01-4 |
| Carb971 | Carbopol 971 | | Noveon | Carbopol 971 | 9003-01-4 |
| Carb974 | Carbopol 974 | | Noveon | Carbopol 974 | 9003-01-4 |
| Carb981 | Carbopol 981 | | Noveon | Carbopol 981 | 9003-01-4 |
| Carb1342 | Carbopol 1342 | | Noveon | Carbopol 1342 | 9003-01-4 |
| Diclo | Diclofenac Sodium | 318.1 | Labochim | | 15307-79-6 |
| DMSO | Dimethyl Sulfoxide (USP) | 78.1 | Gaylord | EM-2951 | 67-68-5 |
| EDTA | Disodium Ethylenediaminetetraacetate Dihydrate | | VWR | MK139504 | 6381-92-6 |
| EtOH | Ethanol (USP) | 46.1 | Spectrum | G1015 | 64-17-5 |
| Gly | Glycerin (USP) | 92.1 | Proctor & Gamble | Superol V | 56-81-5 |
| Guar | Guar gum | | Spectrum | G1044 | 9000-30-0 |
| HEC | Hydroxyethyl cellulose - Natrasol 250M | | Hercules | Natrasol 250M | 9004-62-0 |
| HPMC | Hydroxypropyl methyl cellulose | | Dow Chemical | Methocel E4M | 9004-65-3 |
| HY117 | Hydroxypropyl cellulose | 95,000 | Spectrum | HY117 | 9004-64-2 |
| HY119 | Hydroxypropyl cellulose | 370,000 | Spectrum | HY119 | 9004-64-2 |
| Locu | Locust Bean gum | | Spectrum | L1135 | 9000-40-2 |
| Peg300 | Poly(ethylene glycol) 300 (USP) | ~300 | Spectrum | PO108 | 25322-68-3 |
| PG | Propylene Glycol (USP) | 76.1 | Dow Chemical | | 57-55-6 |
| PVA | Polyvinyl alcohol | 44.1 | Sigma | 81386 | 9002-89-5 |
| PVP | Polyvinyl pyrrolidone | 360,000 | Sigma | 81440 | 9003-39-8 |
| P407 | Polxamer 407 | | Spectrum | P1126 | 9003-11-6 |
| Ultrez10 | Ultrez 10 | | Noveon | Ultrez10 | 9003-01-4 |

The general methodology for preparation of each example provided is as follows, unless otherwise indicated.

Final weight for each formulation was 25 g prepared in 50-mL glass vials. Vortexing or magnetic stir bars were used to mix the gels.

Viscosity was measured at 22° C. using Brookfield DV-III Ultra, programmable Rheometer with LV Spindle #31 at 10 rpm. For stability testing, gels were stored at ambient temperature or in an incubator at 50° C. Discoloration or changes in appearance including phase separation over time were evaluated.

The concentration of the DMSO was consistent in all of the experiments (45.5% w/w). Propylene glycol was at either 11 or 11.2% w/w. Ethanol concentration varied from 11% to 30% w/w. Glycerol concentrations were varied from 0 to 11.2% w/w. The diclofenac sodium concentration was at either 1.5% (w/w) or 2% (w/w). Water was adjusted to compensate for the amount of inactives, thickening agents, and diclofenac sodium present in solution.

Franz diffusion cell experiments were used to analyze diclofenac sodium flux rates of varying gel formulations across a substrate membrane. Franz diffusion cells are a common and well known method for measuring transdermal flux rates. The general Franz cell procedure is described in Franz, T.J., Percutaneous absorption: on the relevance of in vitro data. *J Invest Derm*, 64:190-195 (1975). The following was the methodology used in the present Examples.

Franz cells with a 3 ml receptor well volume were used in conjunction with split thickness cadaver skin (0.015"-0.018", AlloSource). The donor well had an area of ~0.5 cm$^2$. Receptor wells were filled with isotonic phosphate buffered saline (PBS) doped with 0.01% sodium azide. The flanges of the Franz cells were coated with vacuum grease to ensure a complete seal and were clamped together with uniform pressure using a pinch clamp (SS #18 VWR 80073-350). After Franz cells were assembled, the skin was allowed to pre-hydrate for 45 minutes with PBS. PBS was then removed and an appropriate amount of formulation is added to the skin. Dosing levels varied from 2 mg/cm$^2$ (considered finite dose) to 200 mg/cm$^2$ (considered infinite dose). The donor well was then capped to prevent evaporation. Receptor wells of the Franz cells were maintained at 37° C. (temperature on the surface of the skin is ~31° C.) in a stirring dry block with continual agitation via a stir bar. Samples were drawn from the receptor wells at varying time points. Measurements were made in six-fold replicates. The concentration of diclofenac in the samples was analyzed using high performance liquid chromatography. The inventive formulations performed better than the comparator at the limits of finite dosing—finite dosing being a much better predictor of the performance of a formulation in an in vivo situation as opposed to infinite dosing.

A) GEL FORMULATIONS DERIVED FROM A COMPARATIVE LIQUID BASE SOLUTION

Example 2

Gel Formulations Using Various Thickeners in a Comparative Liquid Formulation Base Solution Initially, several thickeners including carbomers, polyvinyl pyrrolidone, locust gum, cellulose polymers and polyvinyl alcohol were tested for their effectiveness at forming a diclofenac sodium gel using the comparative liquid formulation as a base solution. In the gel formulations of this Example, a comparative liquid formulation solution was produced and a thickener was then added directly to this base. In order to facilitate the incorporation of the thickener, sonication and heating (at 60° C.), along with vigorous vortexing/homogenization were performed.

Some thickeners, specifically guar gum, locust bean gum, methocel (HPMC), polyvinyl alcohol, and poloxamer 407 failed to form stable gels. In particular, immediate separation, inefficient thickening, and insolubility of the thickeners was noted. Gels were formed that showed initial stability with several cellulose polymers including hydroxyethyl cellulose (Natrosol HHX) and hydroxypropylcellulose (HY119). Other thickeners that showed an initially stable gel were PVP, and acrylic polymer thickeners.

The specifics of gel formulation for each thickener are provided below:

HEC thickening agents: A lower weight molecular weight hydroxyethyl cellulose (specifically Hydroxyethyl Cellulose (HEC) Type 250 M Pharm (Natrosol®)) was dispersed in the mixture of dimethyl sulfoxide, propylene glycol, glycerine and water and allowed to swell for about 1 hour. Diclofenac sodium was dissolved in ethanol and added to the HEC/solvent blend to obtain a final formulation. Although HEC gels form relatively easily and demonstrate a good flux profile, the gels are yellowish in color and are susceptible to phase separation over extended periods of storage. Table 2 shows the compositions of these formulations, and the resulting flux values of these compositions as compared with a comparative liquid formulation are shown in FIG. 1.

PVP thickening agents: PVP was added at up to 8% w/v after all other components of the comparative liquid base formulation were mixed. PVP gels are clear in nature, but suffer from an undesirable tacky feel when drying. Table 2 and FIG. 1 shows the composition and flux data for this gel. In this example, Franz diffusion cells were dosed at 15 mg per Franz cell. As can be seen in FIG. 1, PVP gels performed reasonably well, but their undesirable aesthetic qualities do not make them ideal for a commercial embodiment.

TABLE 2

Components of HEC and PVP gels used to generate the flux rate data shown in FIG. 1.

| | Formulation name | | | | |
|---|---|---|---|---|---|
| Percentages in | Hec1b wt/wt % | Hec2b wt/wt % | PVP1b wt/wt % | PP54 wt/wt % | Comparative wt/wt % |
| Water | 18.81 | 18.81 | 18.81 | 18.31 | 18.81 |
| Dimethyl Sulfoxide | 45.5 | 45.5 | 45.5 | 45.5 | 45.5 |
| Propylene glycol | 11.2 | 11.2 | 11.2 | 11.2 | 11.2 |
| Ethanol | 11.79 | 11.79 | 11.79 | 11.79 | 11.79 |
| Glycerine | 11.2 | 11.2 | 11.2 | 11.2 | 11.2 |
| Diclofenac Sodium | 1.5 | 1.5 | 1.5 | 2 | 1.5 |
| Thickener | HEC | HEC | PVP | Carbopol 971 | none |
| w/vol % thickener added to solution | 1.1 | 1.3 | 8 | 1 | |

Figure 2:
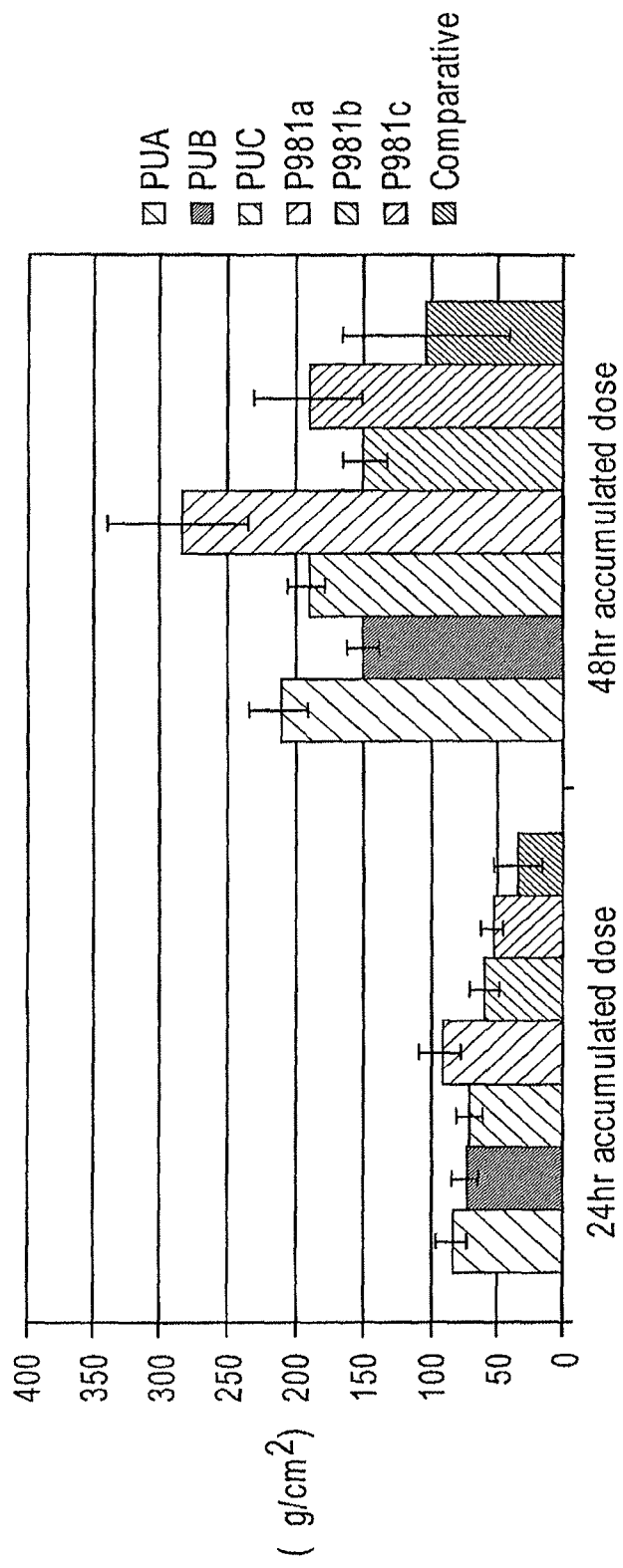
FIG. 2 shows a bar graph of flux rate of gels made with Carbopol 981 and Ultrez 10. Franz diffusion gels were dosed with 200 µl per Franz cell.
Figure 3:
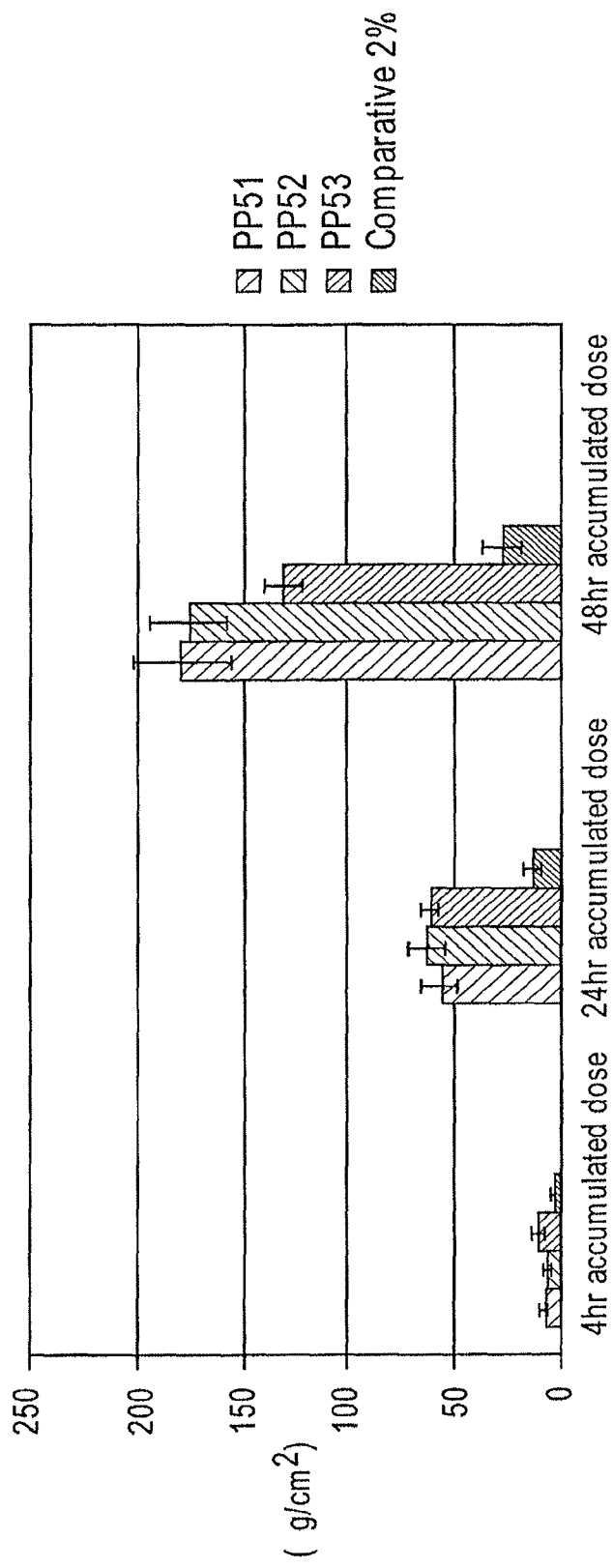
FIG. 3 shows a bar graph of flux rate of carbopol 971 and carbopol 981 gels. Franz diffusion cells were dosed at 50 µl per cell.

Carbopol thickening agents: Carbopol gels were formed by: (1) dispersing an acrylic polymer into a mixture of water, glycerol, and propylene glycol followed by stirring for 1 hour; (2) preparing a second solution of 1.5% diclofenac sodium dissolved in ethanol and DMSO; (3) mixing the diclofenac solution into the carbopol phase. An alternate method for forming carbopol gels is as follows: (1) dispersing the carbopol into dimethyl sulfoxide and stirring for 1 hour; (2) dissolving diclofenac sodium in an ethanol/water/propylene glycol mixture; (3) dispersing glycerol into the diclofenac solution; and (4) mixing the diclofenac solution into the polymer/dimethyl sulfoxide blend, and stirring for 1 hour at ambient temperature. These methods of mixing can be carried out at room temperature, or elevated temperature if desired. Varying carbopols were used to make gels including: Carbopol 1342, 941, 971, 981, 974 and Ultrez 10 (Noveon, Inc.). All carbopol gels were clear, proved stable to both freeze-thaw cycling and incubation at elevated temperature (50° C.) for one month, and had good flow characteristics. Tables 2, 3, and 4 show the composition of these gels, and FIGS. 1, 2, and 3 show their relative flux. A stable and clear gel could be formed at carbopol concentrations of ~>0.3% w/w when making gels with 1.5% w/w diclofenac sodium. For gels with 2% w/w diclofenac sodium, ~>0.9% w/w carbopol was needed to make a stable gel. The exact amount of carbopol needed to from a gel depended on the type of carbopol used.

For the formulations of Table 3, Franz diffusion gels were dosed with 200 μl per Franz cell. Carbopol gels uniformly showed increased flux rates over the comparative formulation (see FIG. 2). Thicker gels (i.e. gels with higher weight percent carbopols) tended to have less flux than a composition with a lower weight percentage of the same carbopol.

TABLE 3

Components of gels made with Carbopol 981 and Ultrez 10 used to generate the flux rate data shown in FIG. 2.

| | Formulation name | | | | | | |
|---|---|---|---|---|---|---|---|
| | PUA | PUB | PUC | P981a | P981b | P981c | Comparative |
| | Percentages in | | | | | | |
| | wt/wt % | wt/wt % | wt/wt % | wt/wt % | wt/wt % | wt/wt % | wt/wt % |
| Water | 18.81 | 18.81 | 18.81 | 18.81 | 18.81 | 18.81 | 18.81 |
| Dimethyl Sulfoxide | 45.5 | 45.5 | 45.5 | 45.5 | 45.5 | 45.5 | 45.5 |
| Propylene glycol | 11.2 | 11.2 | 11.2 | 11.2 | 11.2 | 11.2 | 11.2 |
| Ethanol | 11.79 | 11.79 | 11.79 | 11.79 | 11.79 | 11.79 | 11.79 |
| Glycerine | 11.2 | 11.2 | 11.2 | 11.2 | 11.2 | 11.2 | 11.2 |
| Diclofenac Sodium | 1.5 | 1.5 | 1.5 | 1.5 | 1.5 | 1.5 | 1.5 |
| Thickener | Ultrez | Ultrez | Ultrez | Carb 981 | Carb 981 | Carb 981 | none |
| w/vol % thickener added to solution | 0.90 | 1.03 | 1.16 | .90 | 1.06 | 1.22 | |

Antioxidants and chelating agents can also be added to the carbopol, HEC, or PVP gels. The addition of EDTA to carbopol gels by itself leads to a slightly cloudy gel. BHA gels turned color with incubation at higher temperature. The mixture of BHT and EDTA to carbopol gels did not show any discoloration and remained clear. For the formulations of Table 4, Franz diffusion cells were dosed at 50 μl per cell. FIG. 3 shows flux rates from these gels. Additions of chelating agents and preservatives had no effect on flux rates.

TABLE 4

Components of gels made with carbopol 971 and carbopol 981 gels used to generate the flux rate data shown in FIG. 3.

| | Formulation name | | | |
|---|---|---|---|---|
| Percentages in | PP51 wt/wt % | PP52 wt/wt % | PP53 wt/wt % | Comparative 2% wt/wt % |
| Water | qs | qs | qs | 18.31 |
| Dimethyl Sulfoxide | 45.5 | 45.5 | 45.5 | 45.5 |
| Propylene glycol | 11.2 | 11.2 | 11.2 | 11.2 |
| Ethanol | 11.79 | 11.79 | 11.8 | 11.79 |
| Glycerine | 11.2 | 11.2 | 11.2 | 11.2 |
| Diclofenac Sodium | 2 | 2 | 2 | 2 |
| BHT | 0.1 | | 0.1 | |
| EDTA | 0.05 | | 0.05 | |
| Thickener | Carbopol 971 | Carbopol 971 | Carbopol 981 | none |
| wt/wt % thickener | 1 | 1 | 0.9 | |

B. COMPARATIVE EXAMPLES

Example 3

Comparison of Transdermal Flux of Various DMSO Gel Formulations Versus a Comparative Liquid Formulation A series of diclofenac gel formulations were made wherein the base solution was changed from the comparative base formulation. In particular, the weight percent of propylene glycol, ethanol, glycerine, water, and diclofenac were varied. In these new formulations, the weight percent of the constituent chemicals was as follows: 45.5% DMSO, 20-30% ethanol, 10-12% propylene glycol, 0-4% glycerine, 2% diclofenac sodium, thickener and water added to 100% w/w.

Several thickeners were tested in this new base solution. A number of these thickeners failed to form stable gels; in particular, carbopol gels did not remain stable. However, cellulose gels were uniformly effective at forming gels. The most aesthetically pleasing of these gels was formed with hydroxypropylcellulose (HY117, HY119, HY121). These gels spread easily, were uniform in nature, dried quickly, and demonstrated good flow characteristics.

Hydroxypropylcellulose gels were formed by mixing all the constituent parts and then adding the thickener at the end followed by agitation. The gel can also be formed by dispersing the hydroxypropylcellulose in the aqueous phase prior to solvent addition. Heat can be used to facilitate gel formation. Hydroxypropylcellulose gels were clear and flowed easily. They remain stable for at least six months demonstrating: no phase separation, negligible shift in pH, and low amounts of degradation products (<0.04%). The data in FIGS. 4-9, derived from the formulations of Tables 5-10, indicate that the hydroxypropylcellulose gel formulations of diclofenac sodium of the present invention also provide a transdermal flux rate that is as much as 4-fold higher than a comparative liquid formulation.

Studies were performed to determine the relative transdermal flux of various diclofenac gel formulations of the present invention when compared with a comparative liquid formulation of U.S. Pat. Nos. 4,575,515 and 4,652,557 ("Comparative" in Tables 5-10). Accordingly, the Franz cell procedure described above was used to compare diclofenac flux rates of various diclofenac gel formulations with comparative liquid formulations.

For the formulations of Table 5, Franz cells were dosed at 10 mg per Franz cell. A new gel (F14/2) has an altered base solution over the comparative liquid formulation and demonstrates both faster drying times and better flux kinetics (see FIG. 4). The flux rates for these gels is not as high as the carbopol gels (F971), but the drying rate is substantially faster.

TABLE 5

Figure 4:
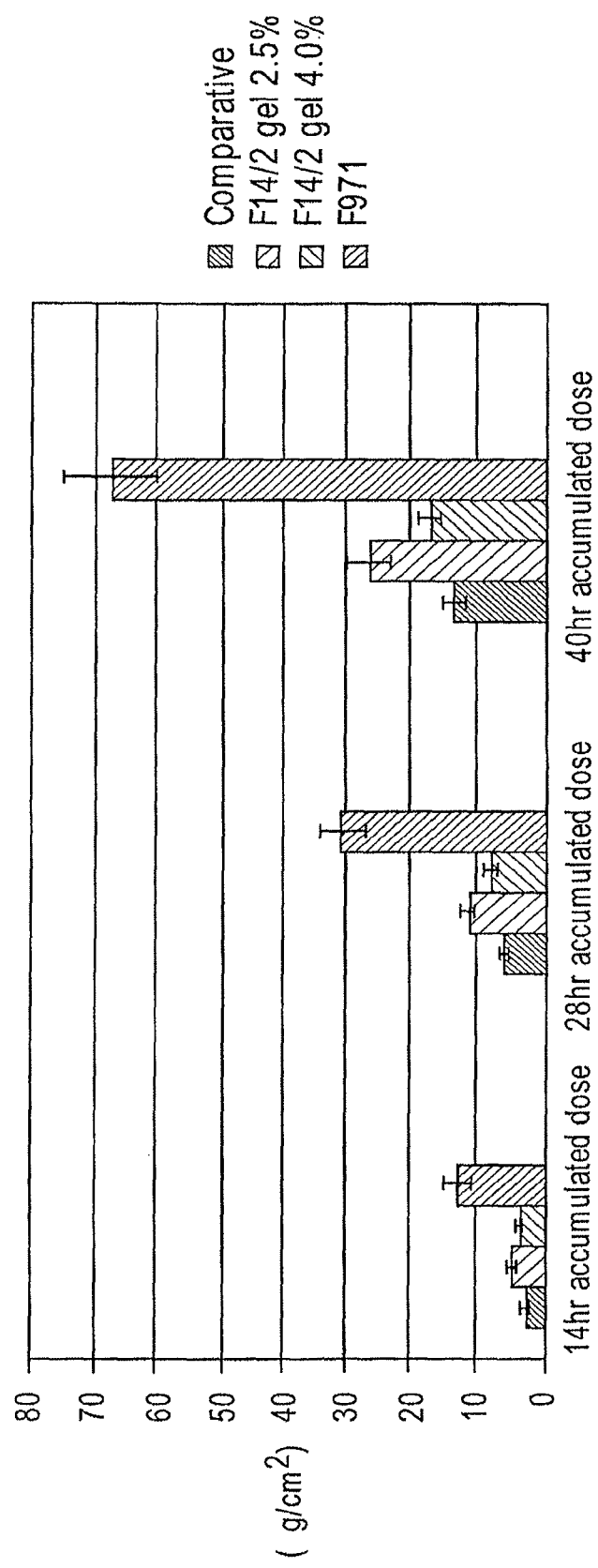
FIG. 4 shows a bar graph of flux rate of various gels and a comparative liquid formulation. Franz cells were dosed at 10 mg per Franz cell.

Components of various gels and a comparative liquid formulation used to generate the flux rate data shown in FIG. 4.

| Percentages in | Comparative wt/wt % | F14/2 gel 2.5% wt/wt % | F14/2 gel 4.0% wt/wt % | F971 wt/wt % |
|---|---|---|---|---|
| Water | 18.81 | 12.5 | 12.5 | 17.16 |
| Dimethyl Sulfoxide | 45.5 | 45.5 | 45.5 | 45.5 |
| Propylene glycol | 11.2 | 11 | 11 | 11.2 |
| Ethanol | 11.79 | 26.5 | 25 | 11.79 |
| Glycerine | 11.2 | | | 11.2 |
| Diclofenac Sodium | 1.5 | 2 | 2 | 2 |
| Thickener | none | HY119 | HY119 | Carbopol 971 |
| wt/wt % thickener | | 2.5 | 4 | 1.15 |

For the formulations of Table 6, Franz diffusion cells were dosed at 7 mg per cell. Lowering the pH shows a marked increase in flux rates (see FIG. 5).

TABLE 6

Figure 5:
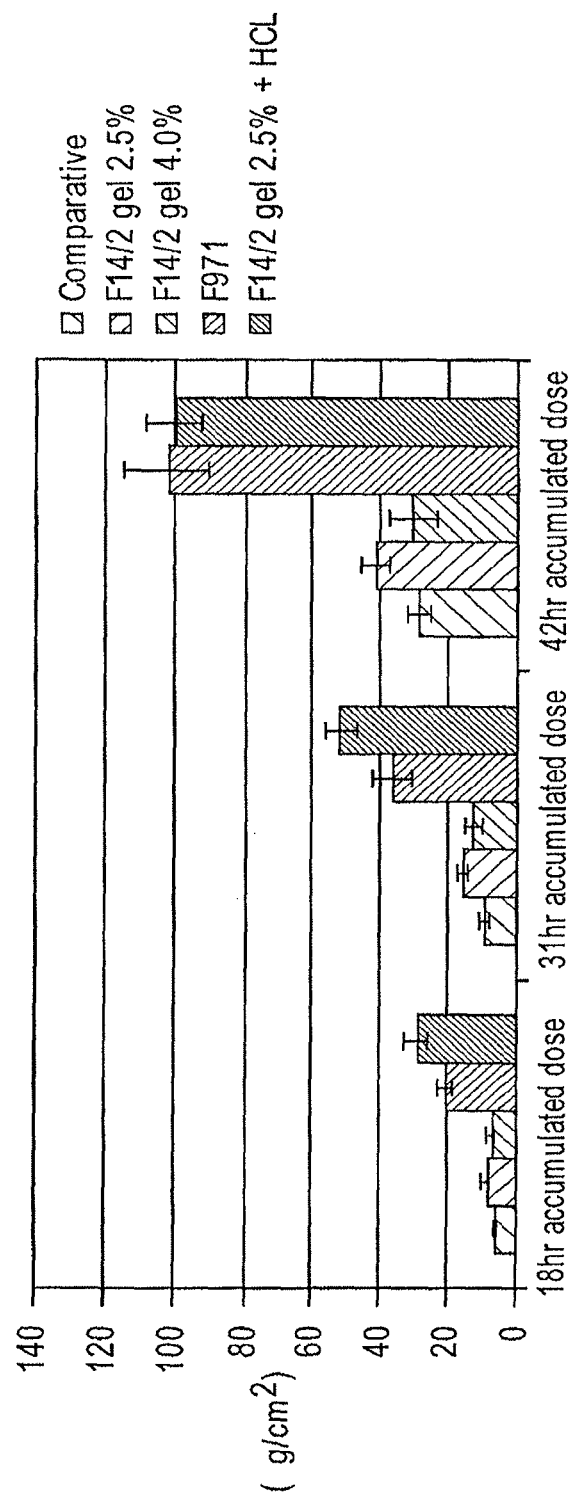
FIG. 5 shows a bar graph illustrating the effect of the pH of various gels and a comparative liquid formulation on flux rate. Franz diffusion cells were dosed at 7 mg per cell.

Components of various gels and a comparative liquid formulation used to generate the flux rate data shown in FIG. 5.

| Percentages in | Comparative wt/wt % | F14/2 gel 2.5% wt/wt % | F14/2 gel 4.0% wt/wt % | F971 wt/wt % | F14/2 gel 2.5% + HCL wt/wt % |
|---|---|---|---|---|---|
| Water | 18.81 | 12.5 | 12.5 | 17.16 | 12.5 |
| Dimethyl Sulfoxide | 45.5 | 45.5 | 45.5 | 45.5 | 45.5 |
| Propylene glycol | 11.2 | 11 | 11 | 11.2 | 11 |
| Ethanol | 11.79 | 26.5 | 25 | 11.79 | 26.5 |
| Glycerine | 11.2 | | | 11.2 | |
| Diclofenac Sodium | 1.5 | 2 | 2 | 2 | 2 |
| concentrated HCL | | | | | *** added to pH 5.3 |
| pH | 9 | 9.43 | 9.67 | 6.77 | 5.3 |
| Thickener | none | HY119 | HY119 | Carb971 | HY119 |
| wt/wt % thickener | | 2.5 | 4 | 1.15 | 2.5 |

For the formulations of Table 7, Franz cells were dosed at 7 mg per Franz cell. The resulting flux rates for each of these formulations is shown in FIG. 6.

TABLE 7

Figure 6:
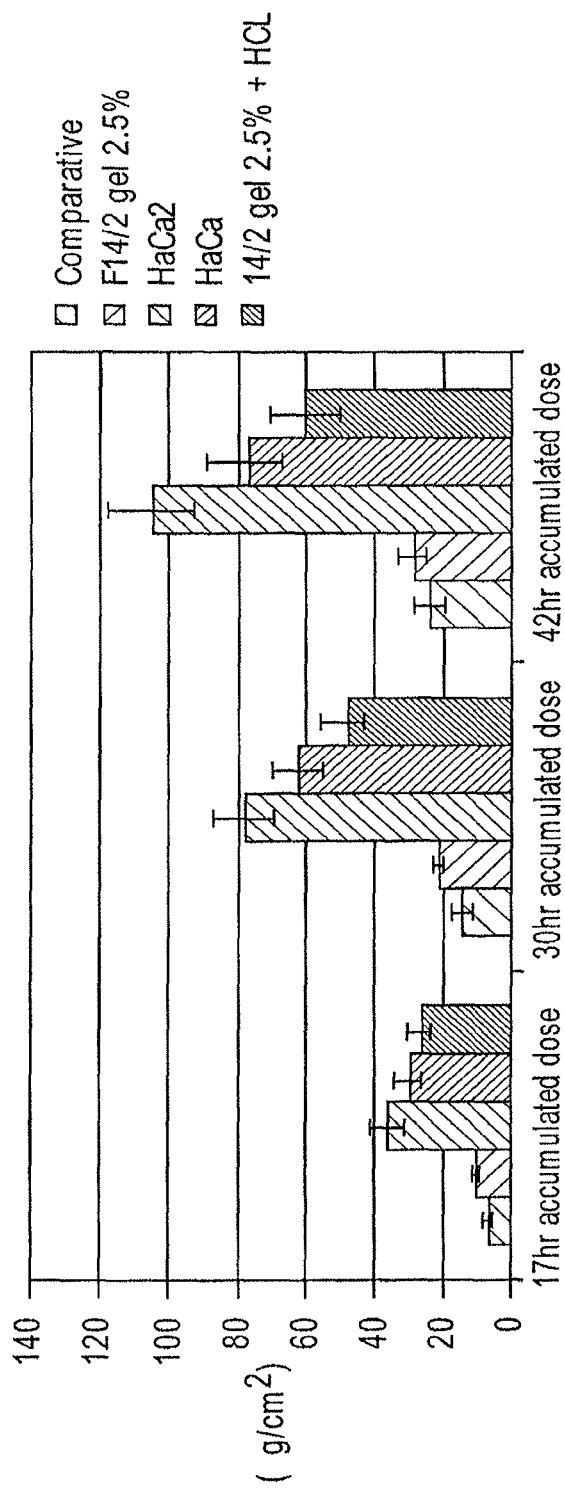
FIG. 6 shows a bar graph of flux rates of various gels. Franz cells were dosed at 7 mg per Franz cell.

Components of various gels used to generate the flux rate data shown in FIG. 6.

| Percentages in | Comparative wt/wt % | F14/2 gel 2.5% wt/wt % | HaCa2 wt/wt % | HaCa wt/wt % | F14/2 gel pH 5.3 wt/wt % |
|---|---|---|---|---|---|
| Water | 18.81 | 12.5 | 22.3 | 26.3 | 12.5 |
| Dimethyl Sulfoxide | 45.5 | 45.5 | 45.5 | 45.5 | 45.5 |
| Propylene glycol | 11.2 | 11 | 11.2 | 11.2 | 11 |
| Ethanol | 11.79 | 26.5 | 12 | 12 | 26.5 |
| Glycerine | 11.2 | | 6 | 2 | |
| Diclofenac Sodium | 1.5 | 2 | 2 | 2 | 2 |
| concentrated HCL | | | | | *** added to pH 5.3 |
| pH | 9 | 9.43 | 6.8 | 6.71 | 5.3 |
| Thickener | none | HY119 | Carbopol 971 | Carbopol 971 | HY119 |
| wt/wt % thickener | | 2.5 | 1 | 1 | 2.5 |

For the formulations of Table 8, the comparative liquid formulation (1.5% diclofenac sodium) was dosed at 20 mg per Franz cell. Solaraze® (a commercially available 3% diclofenac sodium gel) was dosed at 10 mg per Franz cell, and F14/2 was dosed at 15 mg per Franz diffusion cell. At this dosing, all cells were dosed with equivalent amounts of diclofenac sodium. F14/2 continued to show increased performance over other formulations (see FIG. 7).

TABLE 8

Figure 7:
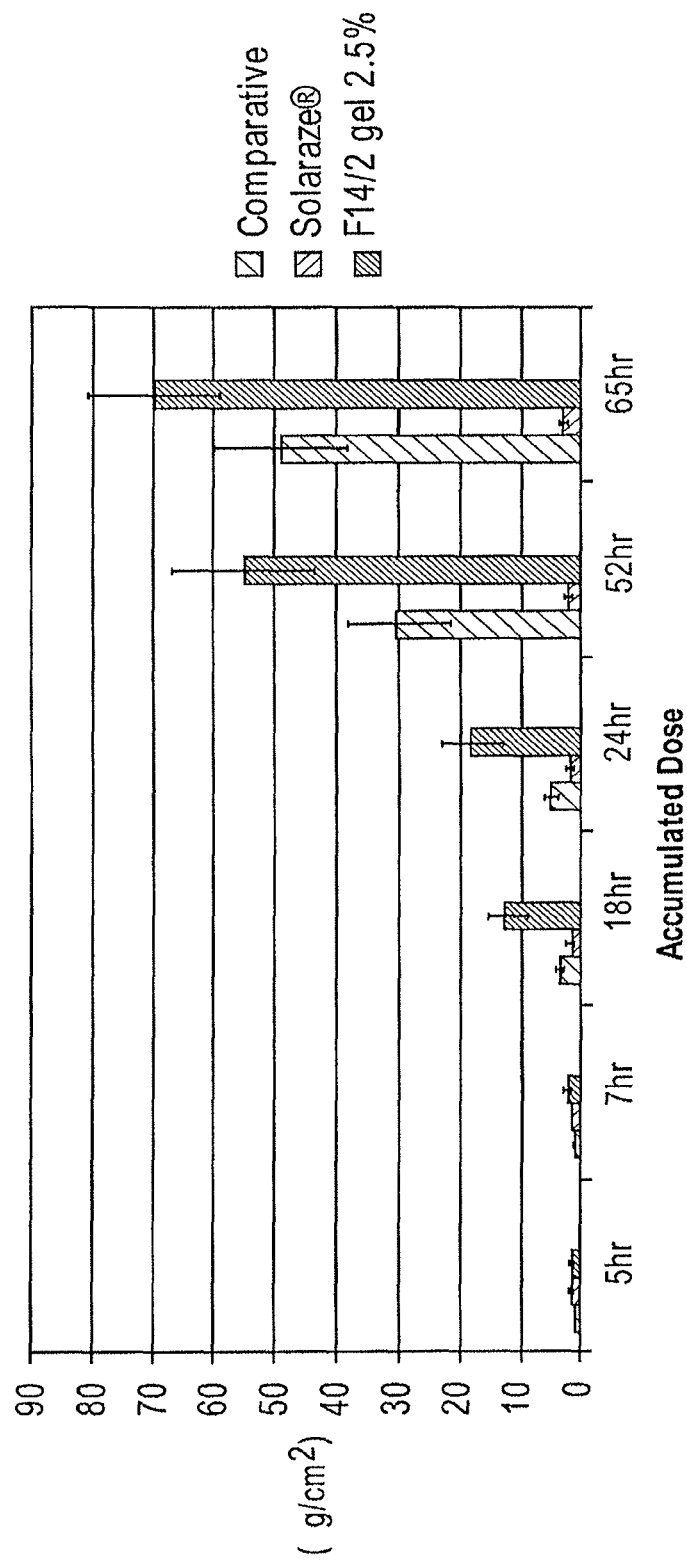
FIG. 7 shows a bar graph of flux rates of various diclofenac formulations. The comparative liquid formulation (1.5% diclofenac sodium) was dosed at 20 mg per Franz cell, Solaraze® (a commercially available 3% diclofenac sodium gel) was dosed at 10 mg per Franz cell, and a formulation of the invention, F14/2, was dosed at 15 mg per Franz diffusion cell. At this dosing, all cells were dosed with equivalent amounts of diclofenac sodium.

Components of various diclofenac formulations used to generate the flux rate data shown in FIG. 7.

| Percentages in | Comparative wt/wt % | Solaraze ® wt/wt % | F14/2 gel 2.5% wt/wt % |
|---|---|---|---|
| Water | 18.81 | | 12.5 |
| Dimethyl Sulfoxide | 45.5 | | 45.5 |
| Propylene glycol | 11.2 | | 11 |
| Ethanol | 11.79 | | 26.5 |
| Glycerine | 11.2 | | |
| Diclofenac Sodium | 1.5 | 3 | 2 |
| Thickener | none | | HY119 |
| wt/wt % thickener | | | 2.5 |

For the formulations of Table 9, the comparative liquid formulation was dosed at 0.9 mg per Franz cell at 0, 4, 8, and 12 hrs. F14/2 was dosed at 1.5 mg per Franz cell at 0 and 6 hrs. The accumulated dose from the gel was considerably higher in comparison to the comparative solution, providing a ~1.5 fold increase in flux (see FIG. 8).

TABLE 9

Figure 8:
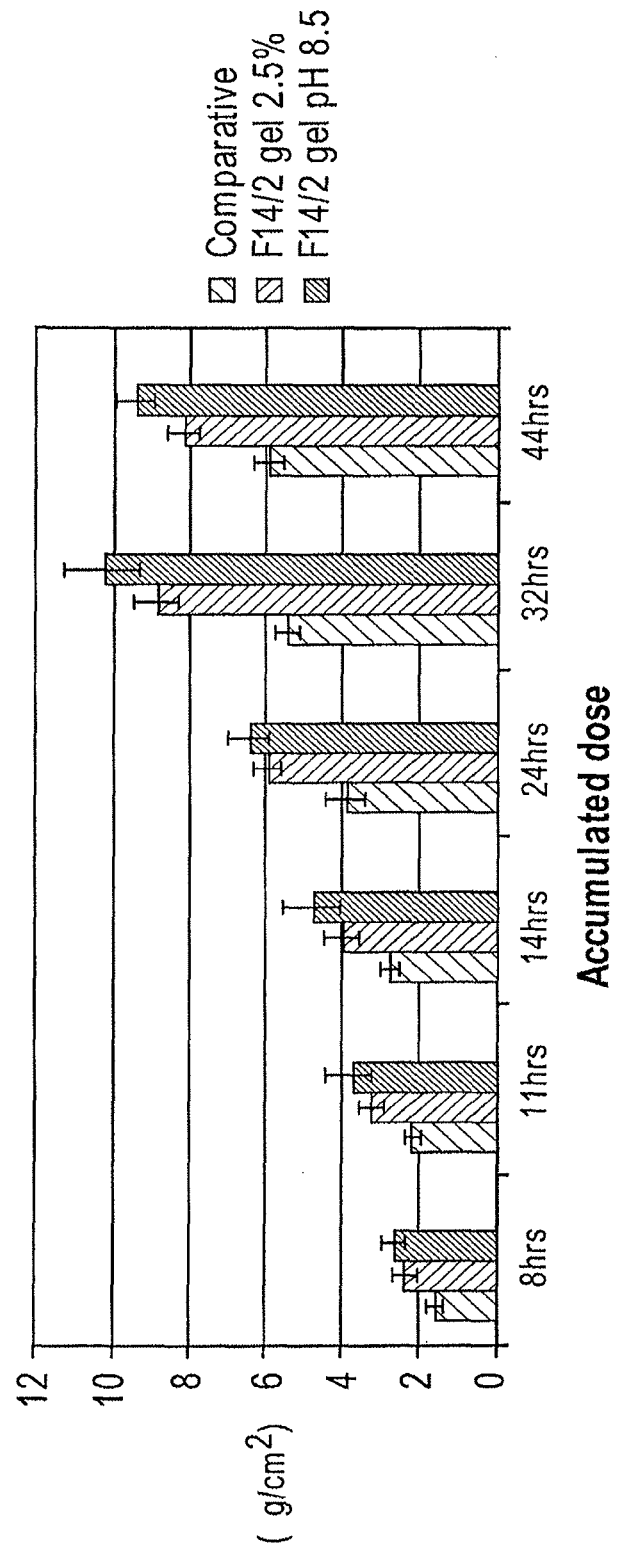
FIG. 8 shows a bar graph of flux rates in multidosing experiments. The comparative liquid formulation was dosed at 0.9 mg per Franz cell at 0, 4, 8, and 12 hrs. A formulation of the invention, F14/2, was dosed at 1.5 mg per Franz cell at 0 and 6 hrs.

Components of formulations used in the multidosing experiments of FIG. 8.

| Percentages in | Comparative wt/wt % | F14/2 gel 2.5% wt/wt % | F14/2 gel pH 8.5 wt/wt % |
|---|---|---|---|
| Water | 18.81 | 12.5 | 45.5 |
| Dimethyl Sulfoxide | 45.5 | 45.5 | 11 |
| Propylene glycol | 11.2 | 11 | 26.5 |
| Ethanol | 11.79 | 26.5 | 12.5 |
| Glycerine | 11.2 | | |
| Diclofenac Sodium | 1.5 | 2 | 2 |
| concentrated HCL | | | *** added to pH 8.5 |
| Thickener | none | HY119 | HY119 |
| wt % thickener | | 2.5 | 4\2.5 |

Figure 9:
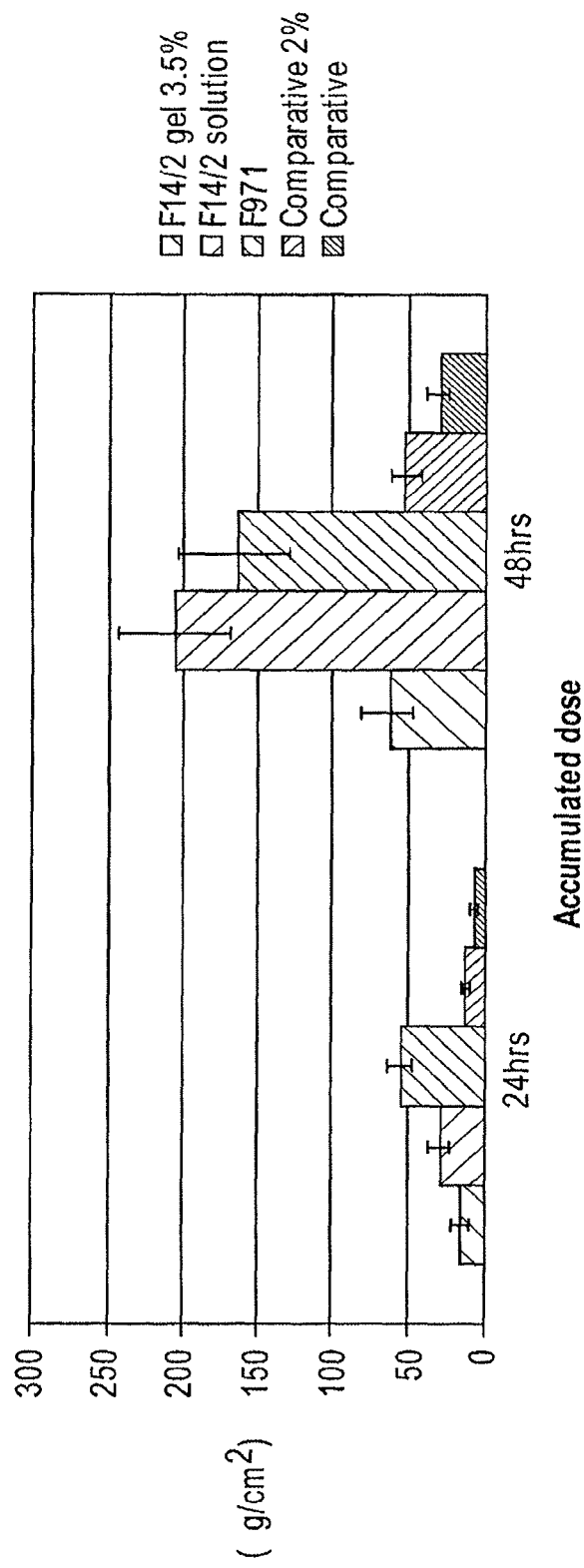
FIG. 9 shows a bar graph of flux rates of various diclofenac formulations. Franz cells were dosed at 20 mg per cell.

For the formulations of Table 10, Franz cells were dosed at 20 mg per cell. The resulting flux rates for these formulations is shown in FIG. 9.

TABLE 10

Flux results from varying diclofenac formulations. Franz cells were dosed at 20 mg per cell.

| Percentages in | F14/2 gel 3.5% wt/wt % | F14/2 solution wt/wt % | F971 wt/wt % | Comparative 2% wt/wt % | Comparative wt/wt % |
|---|---|---|---|---|---|
| Water | 12.5 | 12.5 | 17.16 | 18.31 | 18.81 |
| Dimethyl Sulfoxide | 45.5 | 45.5 | 45.5 | 45.5 | 45.5 |
| Propylene glycol | 11 | 11 | 11.2 | 11.2 | 11.2 |
| Ethanol | 25.5 | 29 | 11.79 | 11.79 | 11.79 |
| Glycerine | | | 11.2 | 11.2 | 11.2 |
| Diclofenac Sodium | 2 | 2 | 2 | 2 | 1.5 |
| Thickener | HY119 | none | Carb 971 | none | none |
| wt/wt % thickener | 3.5 | | 1.1 | | |

Example 4

Comparative Data on Transdermal Flux of Various Diclofenac Gels

Studies were performed to determine the relative transdermal flux of the diclofenac gel formulations of the present invention when compared with previously disclosed formulations, such as the diclofenac diethylamine gel formulation described by Baboota (Baboota et al., *Methods Find. Exp. Clin. Pharmacol.*, 28: 109-114 (2006)). Accordingly, the Franz cell procedure described above was used to compare flux rates of three of the diclofenac formulations described by Baboota with a gel vehicle of the present invention. The diethylamine form of diclofenac was used as the active agent, as that is the form used by Baboota. The exact compositions of the formulations used in this study are shown in Table 11 below. The Baboota formulations are labeled FY1, FY2, and FY3, while a gel formulation using the vehicle of the present invention with diclofenac diethylamine as the active is labeled G14/2 m. A comparative liquid formulation was also included in this study ("Comparative"). Among the primary respect to parameters such as transdermal flux rates, favorable composition consistency, and greater stability and self life) when compared to the previously disclosed diclofenac diethylamine gel formulation described by Baboota or the diclofenac sodium formulation embodied by the Solaraze® gel.

TABLE 11

Figure 10:
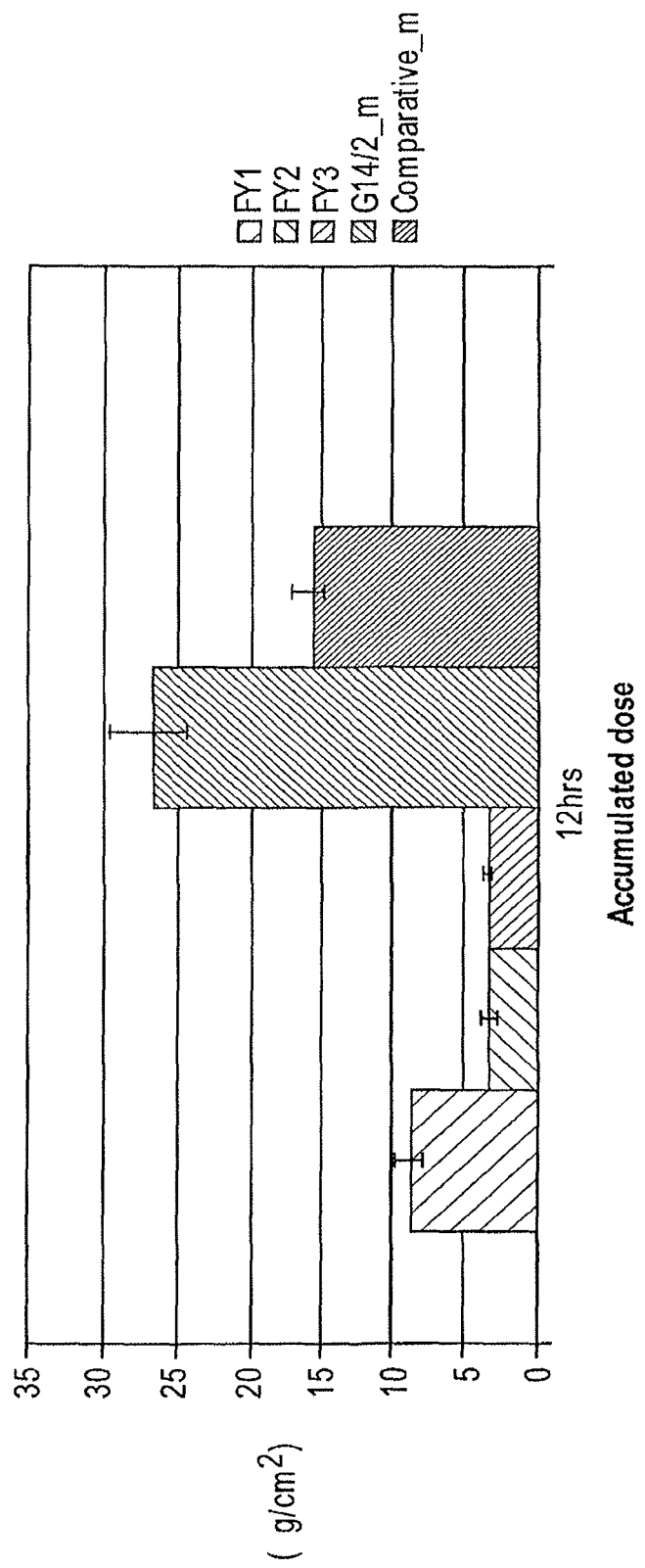
FIG. 10 shows a bar graph of data on diclofenac flux rates from gels disclosed in Baboota et al. and gels of this invention. Franz cells were dosed at 4 mg per cell.

Components of diclofenac diethylamine gels used to generate the flux rate data shown in FIG. 10. For the formulations of Table 11, Franz diffusion cells were finite dosed at 4 mg per cell.

| Percentages in | FY1 wt/wt % | FY2 wt/wt % | FY3 wt/wt % | G14/2_m wt/wt % | Comparative_m wt/wt % |
|---|---|---|---|---|---|
| Dimethyl Sulfoxide | 10 | 10 | 10 | 45.5 | 45.5 |
| Ethanol | 25 | 25 | 25 | 26.5 | 11.79 |
| PEG 400 | 15 | 15 | 15 | | |
| Propylene glycol | 15 | 15 | 15 | 11 | 11.2 |
| triethanolamine DMSO | 0.5 | 0.5 | 0.5 | | |
| Water | qs | qs | qs | 12.5 | 18.81 |
| Sodium carboxymehtylcellulose | | | 6 | | |
| Glycerine | | | | | 11.2 |
| Thickener | Carb 940 | PVA | Carb 940 | HY119 | none |
| wt % Thickener | 1 | 20 | 0.5 | 2.5 | |
| Active: diclofenac diethylamine wt % | 3.4 | 3.4 | 3.4 | 2 | 1.5 | differences between the composition of Baboota's formulation and that disclosed in the present invention is the higher DMSO concentrations in the present formulations (45.5% w/w versus 10% w/w).

As is apparent from the data shown in FIG. 10, although the Baboota formulation is also a gel, the vehicle of the present invention provides a significantly greater flux rate. After 12 hours, the gel of the present invention provides an accumulated dose of 26.8 μg/cm$^2$ versus 8.9 μg/cm$^2$ for Baboota's best performing gel. Thus, the gel of the present invention has a nearly 3-fold greater rate of flux and accumulation of diclofenac than a similar gel, as described by Baboota. Note that these experiments were conducted at finite dosing which is more representative of clinical dosing of a non-occluded composition that is applied periodically but which is not meant to be in continuous contact with the skin. Additionally, the Baboota gels also contained a higher percentage of the active agent, 3.4% w/w as compared to 2% w/w for the compositions using the vehicle of the invention.

Other advantages were also observed, including the consistency and stability of the gel of the present invention when compared with the Baboota gel. In contrast to the smooth and uniform consistency of the present gel, the Baboota gel formulations were cloudy and lumpy, thus, unable to maintain a gel-like consistency. For this reason, the Baboota compositions would be expected to have some stability issues and a short shelf life.

Thus, despite both being gel formulations, when a head-to-head comparison is performed, using a finite dosing protocol, the formulation of the present invention is significantly more effective at the transdermal delivery of a diclofenac active agent, when compared with another gel formulation, that described by Baboota et al. Furthermore, as shown in FIG. 7, the formulation of the present invention also performed remarkably better when compared to a diclofenac gel, Solaraze®, a product currently sold on the market. Thus, the present invention provides a diclofenac sodium gel formulation that has unexpectedly superior properties (e.g., with Example 5

Figure 11:
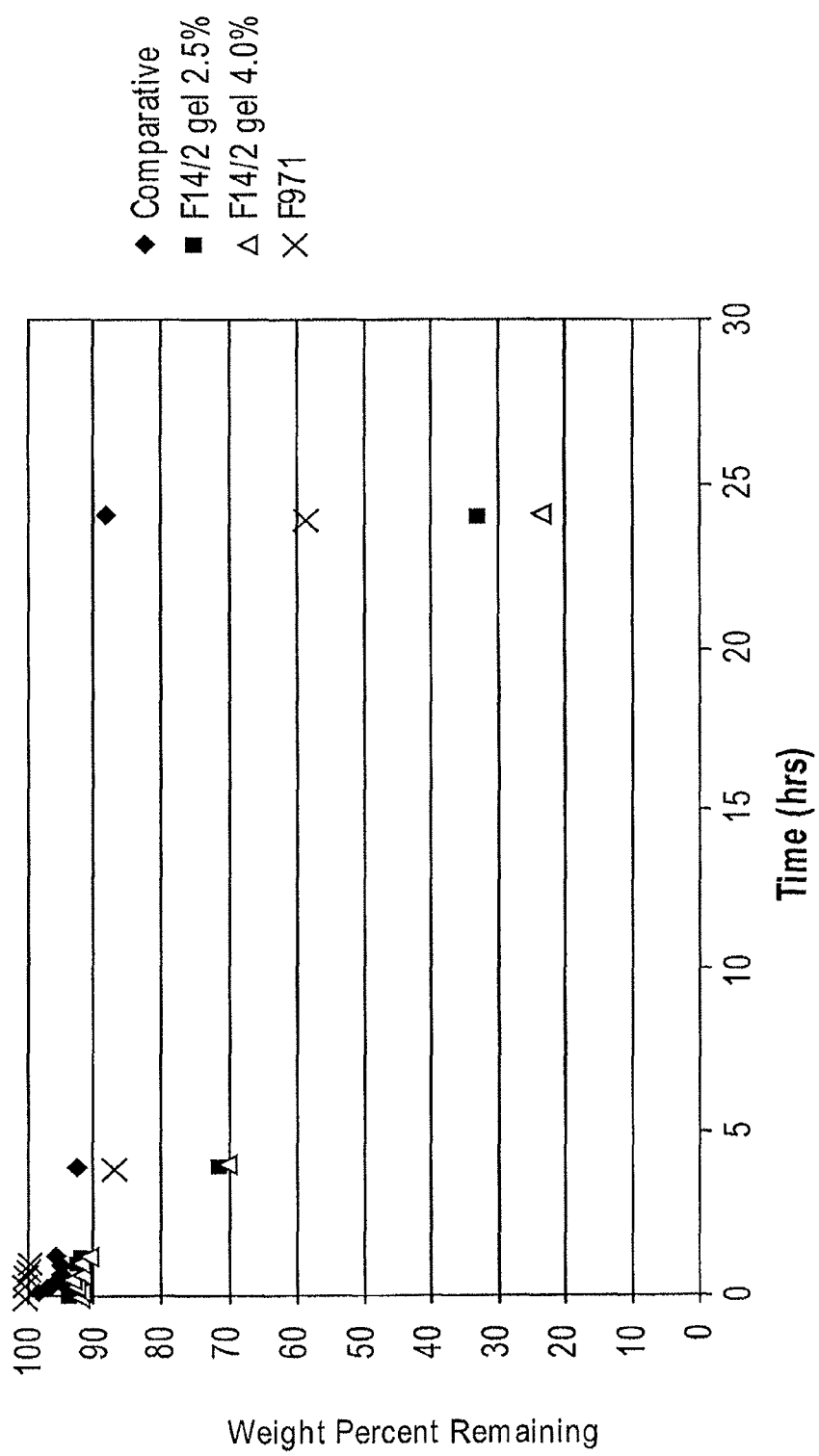
FIG. 11 shows the drying profile over time of three gel formulations and one liquid formulation of diclofenac sodium.

Comparison of Drying Time/Residual Weight of a Comparative Liquid Formulation Solution Versus the Corresponding Gel In order to evaluate the drying time of a comparative liquid formulation solution as compared to the corresponding gel, the study described in this example was performed. Equal weight amounts (100 mg) of either the comparative liquid formulation solution or diclofenac sodium gel formulations were measured on to plastic weigh dishes and spread over a 10 cm$^2$ area, and then left exposed to ambient conditions. At selected time points, the plastic weighing dishes were again weighed to determine the mass of the composition remaining on the weighing dish. As shown by the data in Table 12 below and in FIG. 11, it was surprisingly found that even after a 24 hour drying period, almost all (nearly 90%) of the weight of the initially applied comparative liquid formulation composition remained on the weighing dish. Thus, the weight of the comparative liquid formulation changed very little over the time points measured, indicating that the drying of the liquid formulation occurred very slowly.

In contrast, even within the first five minutes, the three gel formulations displayed more rapid drying than the liquid formulation. 70% of the weight of the two gels that contained 2% or 4% HPC remained, as compared to the over 90% of the liquid formulation which remained, after 4 hours of drying time. By 24 hours, this difference was even more pronounced, as slightly over 20% and 30% of the weight of the two gel formulations containing 2% and 4% HPC, respectively, remained, and slightly under 60% of the weight of the F971 gel remained, as compared to the almost 90% of the liquid formulation which remained. This is a surprising result, as one would have expected the liquid formulation to lose weight more quickly, and thus have a shorter drying time, as compared to a semi-solid gel formulation. Thus, this example demonstrates that the gel compositions of the present invention display superior drying characteristics as compared to a comparable liquid formulation.

Thus, in certain embodiments, the present invention provides a formulation which has a drying time such that, at most, a 50% weight of the starting amount remains as a residue after 24 hours of drying time, preferably a 30-40% or less weight of the starting amount remains as a residue after 24 hours of drying time.

The improved drying time of the gel formulations of the present invention provides improved ease of use and is expected to lead to better patient compliance. Thus, this invention provides a gel formulation with improved drying characteristics while also providing improved drug delivery, as evidenced by the advantageous transdermal flux data shown in the examples above.

TABLE 12

Drying times for gels and a comparative liquid formulation solution. Equal weights of each formulation were measured and spread on weigh dishes. The weight of each remaining formulation was then followed with time. The gels of this invention showed faster drying kinetics than the comparative liquid formulation, with F14/2 showing the fastest drying rate. These gels also had improved "spreadability" characteristics, which most likely contributed to this improvement in drying rates. Drying times

| Percentages in | Formulation name | | | |
|---|---|---|---|---|
| | Comparative wt/wt % | F14/2 gel 2.5% wt/wt % | F14/2 gel 4.0% wt/wt % | F971 wt/wt % |
| Water | 18.81 | 12.5 | 12.5 | 17.16 |
| Dimethyl Sulfoxide | 45.5 | 45.5 | 45.5 | 45.5 |
| Propyelene glycol | 11.2 | 11 | 11 | 11.2 |
| Ethanol | 11.79 | 26.5 | 25 | 11.79 |
| Glycerine | 11.2 | | | 11.2 |
| Diclofenac Sodium | 1.5 | 2 | 2 | 2 |
| Thickener | none | HY119 | HY119 | Carbopol 971 |
| wt/wt % thickener | 3.5 | 2.5 | 4 | 1.15 |

| | % Remaining | | | |
|---|---|---|---|---|
| Time (hr) | Comparative | F14/2 gel 2.5% | F14/2 gel 4.0% | F971 |
| 0.000 | 100 | 100 | 100 | 100 |
| 0.083 | 98.1 | 93 | 92.6 | 100.3 |
| 0.167 | 96.7 | 92.9 | 91.8 | 100.3 |
| 0.333 | 95.7 | 92.7 | 93 | 100.2 |
| 0.500 | 95.6 | 92.7 | 93.3 | 100 |
| 0.750 | 95.5 | 92.1 | 92.3 | 99.8 |
| 1.000 | 95.9 | 92 | 91.8 | 99.7 |
| 4.000 | 93 | 71 | 70.7 | 86.8 |
| 24.000 | 88.7 | 32.4 | 23.5 | 58.8 |

Example 6

Comparison of Stability Characteristics of a Comparative Liquid Formulation Versus Diclofenac Sodium Gel Formulations This example provides a comparison of the stability of the compositions of the present invention tested against reference formulations at room temperature over a six month period. It was unexpectedly found that while the compositions of the invention contain a higher concentration of active agent, they in fact resulted in a lower concentration of a degradation impurity as compared to the reference. It was also unexpectedly found that compositions using hydroxypropylcellulose (HPC) as the gelling agent had a significantly lower quantity of this impurity as compared to compositions made using carbomer gelling agents.

In this study, samples of the test compositions were placed into plastic screw cap bottles which were sealed and held at 25° C. at 60% humidity for 6 months. After the 6 month storage period, the samples were tested for impurities by high performance liquid chromatography (HPLC). The active agent, diclofenac sodium, was found to elute by HPLC with an elution time of about 11 minutes. It was found that upon 6 months of storage, an impurity, termed "impurity A", was seen to elute at about 6.6 minutes in varying amounts for the various compositions as shown in Table 13 below.

TABLE 13

| Composition | Percent "impurity A" after 6 months of storage (wt/wt) |
|---|---|
| 1.5% diclofenac sodium as a comparative liquid formulation solution | 0.034% |
| 2.0% diclofenac sodium in 0.9% Carbopol gel | 0.09% |
| 2.0% diclofenac sodium in 3.5% HPC gel | 0.02% |

Thus, as indicated by the data in Table 13, while having a higher concentration of the active agent, diclofenac sodium, a gel formulation of the present invention containing 3.5% HPC shows a higher degree of stability, as reflected in the appearance of a lower percentage of "impurity A" as compared to a comparable liquid formation. The data shown in Table 13 also shows that the HPC gel formation is more stable than a comparable gel formation containing 0.9% Carbopol, as the HPC gel formation demonstrates an at least 4-fold reduction in the level of impurity A. Thus, a gel formation of the present invention provides improved stability of the active agent as compared to the reference formulations as evidenced in a formulation which degrades by less than 0.034% or 0.09%, over 6 months, as was observed for the reference formulations. Furthermore, the amount of "impurity A" found in the gel formulation of the present invention after a 6 month storage period would result in an exposure level well below limits that would require additional nonclinical testing testing of the impurity.

Example 7

Comparison of in vivo Epicutaneous Absorption of Liquid Versus Gel Formulations

A study was conducted to compare systemic absorption after topical application (also referred to as epicutaneous absorption) of a comparative solution with a gel of the invention. A parallel design was employed with 6 Landrace pigs per arm. Drug was applied for 7 days with an additional dose on Day 8. Blood was sampled on Day 1 to determine a baseline; Day 6, Day 7 and Day 8 samples were taken to confirm steady state, and additional samples were taken at 0 hr, 2 hr, 5 hr, 7 hr, 12 hr, 15 hr, and 24 hr on Day 7 to determine a 24 hour steady state profile; samples taken from Days 8-13 were used to determine an elimination profile.

The doses used in this study were as follows: The comparative solution group received 3.85 mg diclofenac sodium per administration and animal 4 times daily; the gel Group received 8.08 mg diclofenac sodium per administration and animal 2 times daily; the administration area was 5 cm×10 cm/ animal. These amounts represent the scaled human clinical doses.

Sufficient blood was collected from each animal per sampling time and processed for at least 2 mL Li-Heparin plasma/ sample, which were split into two aliquots of 1 mL each. Blood was withdrawn from all animals as shown in Table 14.

TABLE 14

Blood sampling 28

| Test Day(s) | Sampling times | No. of samples | No. of aliquots |
|---|---|---|---|
| 1 | 0 (prior to first administration) | 24 | 48 |
| 6 | 0 (prior to first administration), | 24 | 48 |
| 7 | 0 (prior to first administration), 2 hr post first dosing, 5 hr post first dosing (prior to second administration for Group 1), 7 hr post first dosing, 10 hr post first dosing (prior to third administration for Group 1 and prior to second administration for Groups 2, 3, and 4.) 12 hr post first dosing 15 hr post first dosing (prior to fourth administration for Group 1) | 168 | 336 |
| 8-13 | 0 (pre-dose), 4, 8, 12, 24, 48, 72, 96, and 120 hr post administration | 216 | 432 |
| Total number of samples | | 432 | 864 |

Pharmacokinetic evaluation of the plasma data was performed using TopFit 2.11. A non-compartment model was used for the calculation of the terminal half life and area under the curve (AUC). Elimination rate constants ($K_{el}$) and plasma elimination half-lives ($t_{1/2}$) were calculated by linear regression analysis of the log/linear portion of the individual plasma concentration-time curves (c=concentration, t=time). Half-life was determined using the formulae:

$$t_{1/2} = ln2/K_{el} [h]$$

$$dc/dt = (K_{el})(c)[h]$$

Area under the curve (AUC) values were calculated using the linear trapezoidal method and extrapolated to infinite time by dividing the last measurable plasma concentration by the terminal elimination rate constant. Plasma concentrations at time zero were taken to be those at the pre-dose blood sampling time on Test Day 8. Area under the curve (AUC) was calculated using the formula:

$$AUC = \int c\, dt\, (ng/mL)(h), \text{ integrated from zero to infinity.}$$

The following pharmacokinetic parameters for diclofenac sodium were calculated:

$AUC_{0-24}$ (Test Day 7)

$AUC_{0-t}$ (Test Day 8)

$AUC_{0-inf}$ (Test Day 8)

$T_{max}$ (Test Days 7, 8) (time to reach $C_{max}$)

$C_{max}$ (Test Days 7, 8) (maximum observed plasma concentration)

$C_{min}$ (Test Days 7, 8) (minimal observed plasma concentration)

$C_{(trough)}$ (Test Days 6, 7, and 8) (trough plasma concentration)

$K_{el}$ (elimination half-life)

$T_{1/2}$ (plasma elimination half-life).

The achievement of steady state was assessed by using repeated measures ANOVA with log-transformed trough concentrations on Test Days 6, 7, and 8 as the dependent variable, time as the independent variable, subject as a random effect, and day as a fixed effect.

Figure 12:
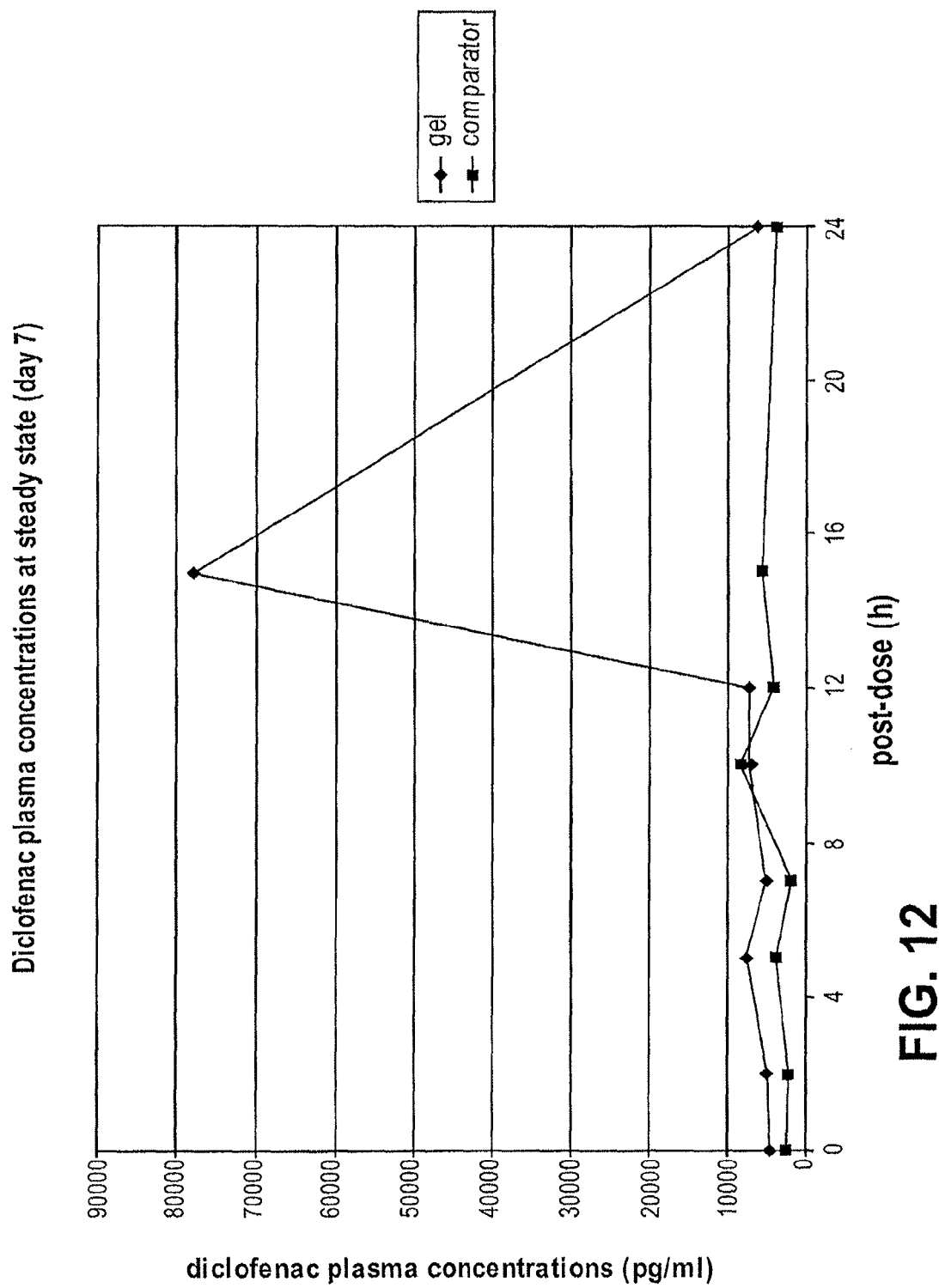
FIG. 12 shows the in vivo steady state plasma concentrations of diclofenac sodium after administration of either a liquid or gel formulation.

The data is shown in FIG. 12 and Tables 16 and 17. Compositions of the invention show significantly more absorption of diclofenac sodium as measured by the mean AUC. This result holds even when adjusting for dose.

TABLE 15

Dosing in pigs

| | Diclofenac Sodium % (w/w) | Area of application (cm²) | Dose of the product per application (mL) | Diclofenac Sodium per dose (mg) | Number of doses per day | Diclofenac per day (mg) |
|---|---|---|---|---|---|---|
| Gel | 2.0 | 50 | 0.40 | 8.08 | bid | 16.2 |
| Comparative Solution | 1.5 | 50 | 0.24 | 3.85 | qid | 15.4 |

TABLE 16

PK profile at steady state on Day 7

| treatment | subject | Tmax (h) | Cmax (pg/ml) | AUC 0-24 (pg * h/ml) |
|---|---|---|---|---|
| Gel | 13 | 12 | 15379 | 239818 |
| | 14 | 10 | 8570 | 175862 |
| | 15 | 5 | 6014 | 104122 |
| | 16 | 5 | 4827 | 63842 |
| | 17 | 15 | 434829 | 2689765 |
| | 18 | 24 | 14484 | 231494 |
| | Mean | 12 | 80684 | 584151 |
| | SD | 7 | 173549 | 1033866 |
| Comparative Solution | 1 | 10 | 8302 | 107122 |
| | 2 | 10 | 24709 | 133521 |
| | 3 | 15 | 14743 | 160294 |
| | 4 | 0 | 4350 | 44267 |
| | 5 | 24 | 9552 | 112460 |

TABLE 16-continued

PK profile at steady state on Day 7

| treatment | subject | Tmax (h) | Cmax (pg/ml) | AUC 0-24 (pg * h/ml) |
|---|---|---|---|---|
| | 6 | 12 | 8628 | 77881 |
| | Mean | 12 | 11714 | 105924 |
| | SD | 8 | 7185 | 40865 |

TABLE 17

Relative bioavailability and exposure to a comparative liquid formulation in comparison to the corresponding gel at steady state

| | Ratio Gel/Comparative Solution % |
|---|---|
| $C_{max}$ | 167.7 |
| $C_{max}$/Dose | 161.5 |
| AUC 0-24 | 241.1 |
| AUC 0-24/Dose | 232.2 |

Example 8

Clinical Trials of Diclofenac Gel in the Treatment of Osteoarithritis

A clinical trial will be performed to evaluate the safety and efficacy of a gel formulation of the present invention in subjects with symptoms of primary osteoarthritis (OA) of the knee. Specifically, a 2-arm, double-blinded, placebo-controlled, randomized, 12-week Phase III clinical trial will be performed in 300 subjects randomized to receive either a diclofenac gel formulation, placebo gel (the gel carrier containing no diclofenac). Subjects will apply 2 mL of study gel to their OA knee per application.

The primary variables for assessment of efficacy will be the WOMAC LK3.1 pain and physical function and Patient Overall Health Assessment. Secondary variables will be the WOMAC stiffness and Patient Global Assessment. The primary efficacy analyses will be the comparison of the change from baseline to final assessment of the primary efficacy variables for subjects in the diclofenac sodium gel arm versus the placebo gel arm.

More specifically, the efficacy of diclofenac gel on knee OA symptoms will be measured by the subjective response of subjects as determined by an efficacy variables questionnaire which includes the WOMAC LK3.1 OA Index (pain, physical function, and stiffness dimensions), a Patient Overall Health Assessment, and a Patient Global Assessment. (See Bellamy, N., WOMAC Osteoarthritis Index User's Guide IV, Queensland, Australia (2003)).

The WOMAC LK3.1, Patient Overall Health Assessment and Patient Global Assessment questionnaires will be based on the five-point Likert scale. Numerical values will be assigned to WOMAC LK3.1 scores, Patient Global Assessment scores and Patient Overall Health Assessment scores, as follows:
Patient Overall Health Assessment and WOMAC LK3.1
Patient Global Assessment
None=0 Very Good=0
Mild=1 Good=1
Moderate=2 Fair=2
Severe=3 Poor=3
Extreme=4 Very Poor=4.

The WOMAC LK3.1 OA Index is a segregated, multidimensional, self-administered index with three independent dimensions: pain, stiffness and physical function and will be used as an efficacy variable in this study.

In a preferred embodiment of the invention, application of the gel formulations of the invention when applied topically will result in a reduction of pain or physical function on the WOMAC scale of at least 1 Likert scale unit over a 12 week period. Even more preferably, a reduction of 2, 3, or 4 Likert scale units will result. Most preferably, application of the gel formulations of the invention will result in complete relief of pain and complete or nearly complete restoration of physical function.

To assess safety, the frequency of adverse effects will be tabulated, the worst skin irritation score will be documented, and change in vital signs and laboratory parameters will be assessed.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable, and/or equivalent structures, functions, ranges, or steps to those claimed, whether or not such alternate, interchangeable, and/or equivalent structures, functions, ranges, or steps are disclosed herein, and without intending to publicly dedicate any patentable subject matter.

All publications, patents and patent applications referred to herein are incorporated by reference in their entirety to the same extent as if each individual publication, patent or patent application was specifically and individually indicated to be incorporated by reference in its entirety.

What is claimed is:

1. A topical formulation consisting of:
diclofenac sodium present at 2% w/w;
DMSO present at 40 to 50% w/w;
hydroxypropyl cellulose;
ethanol present at 23% to 29% w/w;
propylene glycol present at 10% to 12% w/w; and
water to make 100% w/w,
wherein the topical formulation has a viscosity of 500 to 5000 centipoise, and
wherein the formulation has a pH of 4 to 10.

2. The topical formulation of claim 1, wherein the concentration of DMSO is 45.5% w/w.

3. The topical formulation of claim 1, wherein the concentration of the propylene glycol is 10% w/w.

4. The topical formulation of claim 2, wherein the concentration of the propylene glycol is 11% w/w.

5. The topical formulation of claim 2, wherein the concentration of the propylene glycol is 12% w/w.

6. The topical formulation of claim 1 wherein the concentration of the hydroxypropyl cellulose is 2.5% w/w.

7. The topical formulation of claim 1, wherein the viscosity is at least 1000 cp.

8. The topical formulation of claim 2, wherein the viscosity is at least 1000 cp.

9. The topical formulation of claim 1, wherein the formulation degrades at less than 1% over 6 months.

10. The topical formulation of claim 2, wherein the formulation degrades at less than 1% over 6 months.

11. A method for treating pain due to osteoarthritis of a knee of a patient in need thereof comprising administering to the knee a topical formulation of claim 1.

12. The method of claim 11, wherein the formulation is topically administered to the knee 2 times per day.

13. A method for treating pain due to osteoarthritis of a knee of a patient in need thereof comprising administering to the knee a topical formulation of claim 2.

14. The method of claim 13, wherein the formulation is topically administered to the knee 2 times per day.

* * * * *